United States Patent [19]

Tamaki

[11] Patent Number: 4,588,270

[45] Date of Patent: May 13, 1986

[54] CURVATURE MEASURING APPARATUS

[75] Inventor: Hiroshi Tamaki, Tokyo, Japan

[73] Assignee: Tokyo Kogaku Kikai Kabushiki Kaisha, Tokyo, Japan

[21] Appl. No.: 436,853

[22] Filed: Oct. 26, 1982

[30] Foreign Application Priority Data

Oct. 28, 1981 [JP] Japan .................. 56-173529

[51] Int. Cl.$^4$ ............................. A61B 3/10
[52] U.S. Cl. .................... 351/212; 351/247
[58] Field of Search ................. 351/212, 247

[56] References Cited

U.S. PATENT DOCUMENTS

| | | | |
|---|---|---|---|
| 2,174,308 | 9/1939 | Hartinger | 351/212 |
| 3,108,523 | 10/1963 | Nuchman et al. | 351/212 |
| 3,544,220 | 12/1970 | Kaye | 351/212 |
| 3,880,525 | 4/1975 | Johnson . | |
| 4,159,867 | 7/1979 | Achatz et al. . | |
| 4,439,025 | 3/1984 | Smirmaul | 351/212 |

FOREIGN PATENT DOCUMENTS

| | | |
|---|---|---|
| 54-160271 | 12/1979 | Japan . |
| 56-188371 | 2/1981 | Japan . |
| 56-66235 | 6/1981 | Japan . |
| 57-31837 | 2/1982 | Japan . |

Primary Examiner—Rodney B. Bovernick

Attorney, Agent, or Firm—Brumbaugh, Graves, Donohue & Raymond

[57] ABSTRACT

A curvature measuring apparatus is provided for measuring the radii of curvature of a curved surface, particularly a human cornea or a contact lens. The apparatus comprises an illuminating optical system which illuminates the surface to be measured. The optical system includes a light source for forming a pattern of radiating beams of at least two groups, with each group being comprised of at least two parallel straight lines in a virtual plane. The straight lines in one group are different in directions of arrangement from the straight lines in the other group, and each group includes at least one line whose characteristics are substantially different from the other lines in the group to serve as a reference line. A collimator lens orients principal rays of illuminating beams of light emitted from the light source through a pin hole arranged on an optical axis, to be parallel to the optical axis so as to illuminate the surface to be measured by the illuminating beams of light. A detector is provided which is positioned in a virtual plane which is afocal with the plane containing the light source, for detecting the illuminating beams of light reflected from the surface. An arithmetic calculator calculates a radius of curvature of the surface from changes in inclination and pitch which are produced between a pattern of projected straight lines and the pattern of radiating beams from the light source.

29 Claims, 51 Drawing Figures

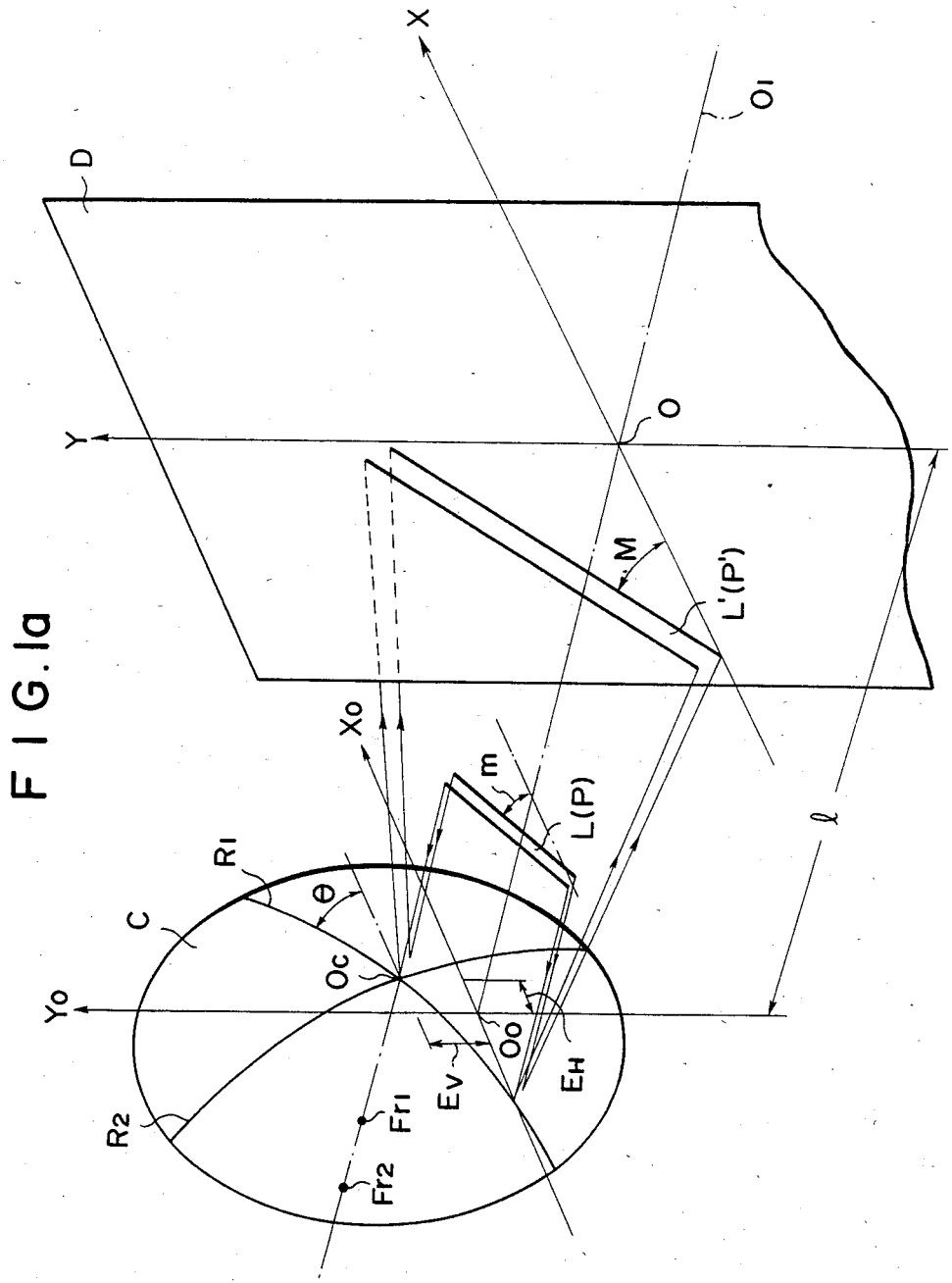

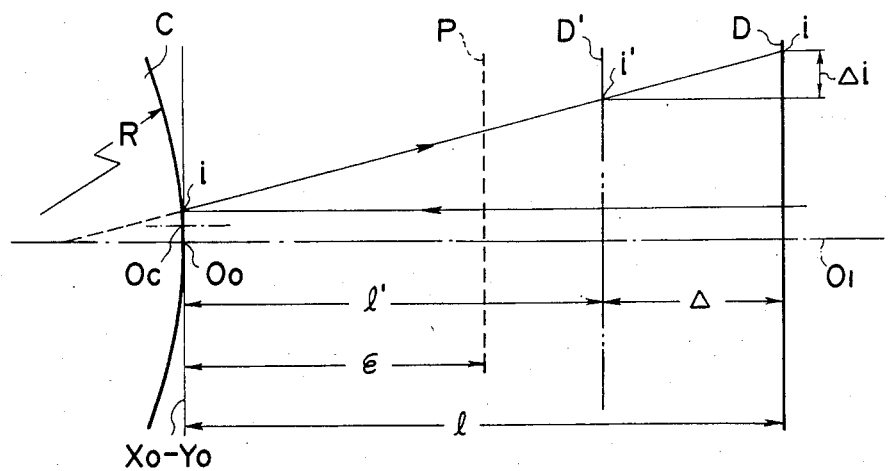
F I G. 1b
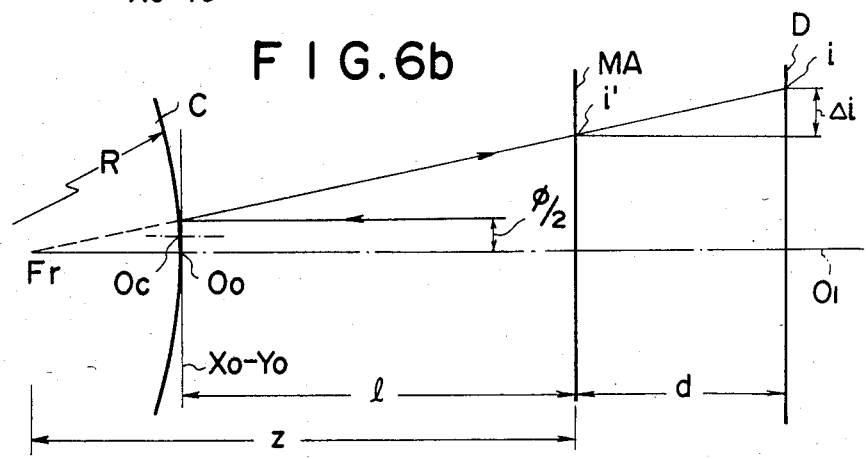
F I G. 6b
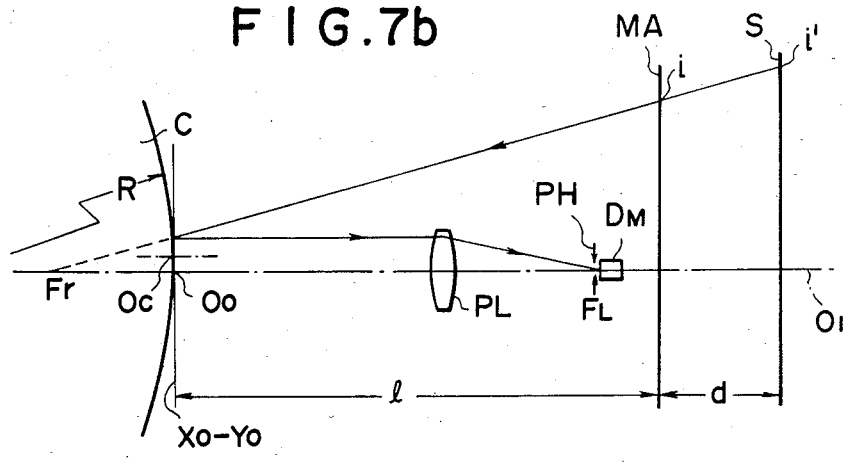
F I G. 7b

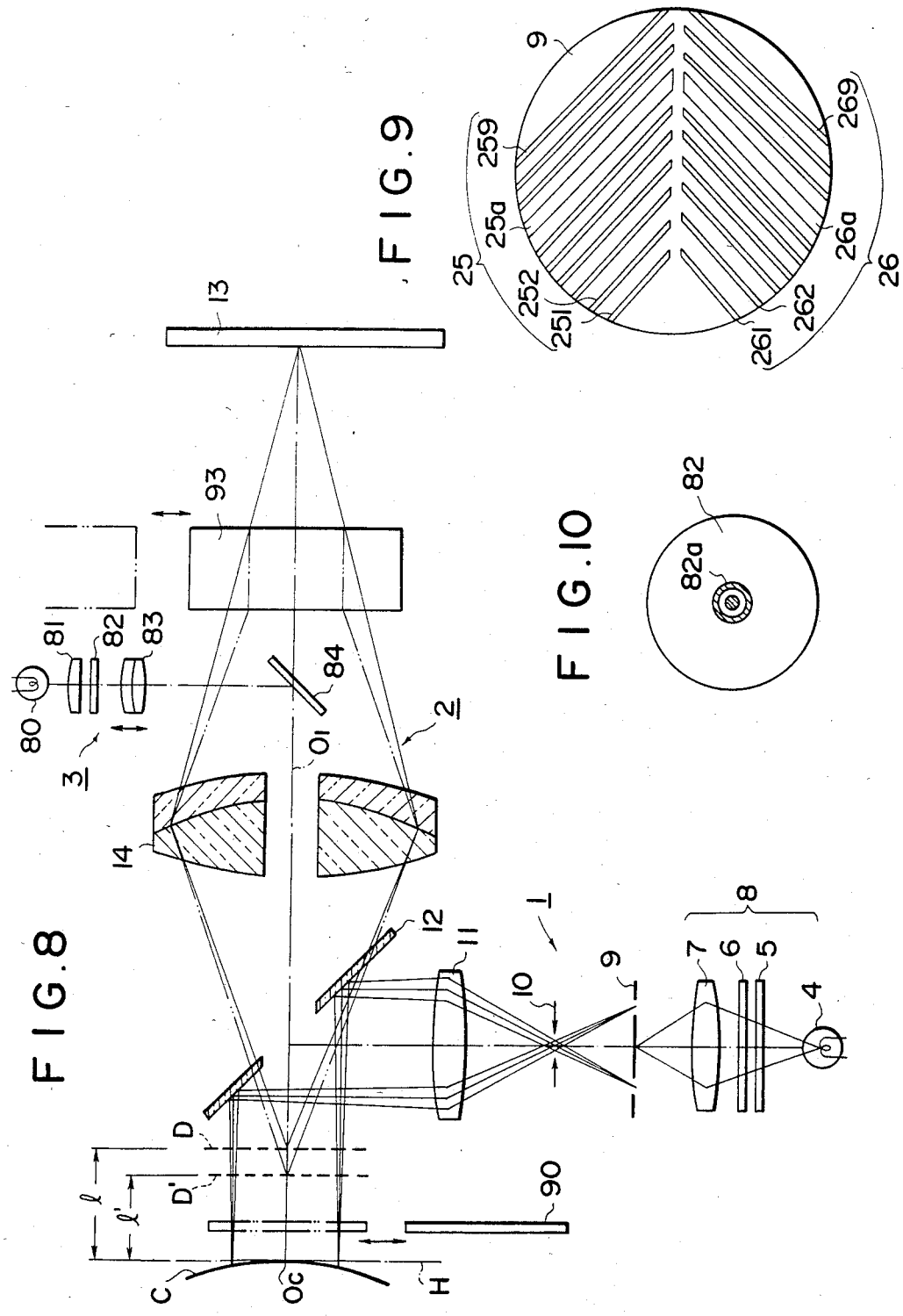

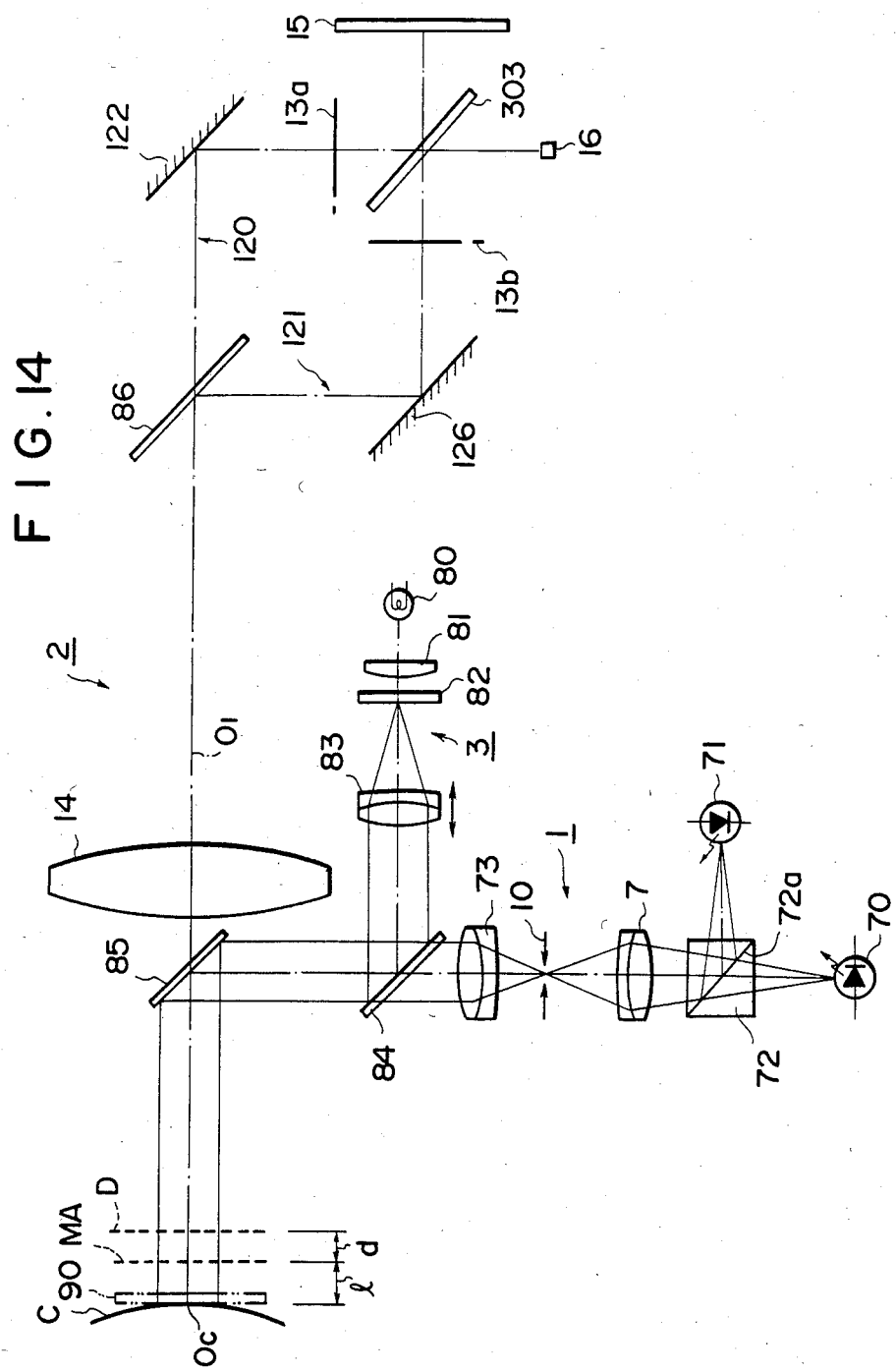

FIG. 15a
FIG. 15b
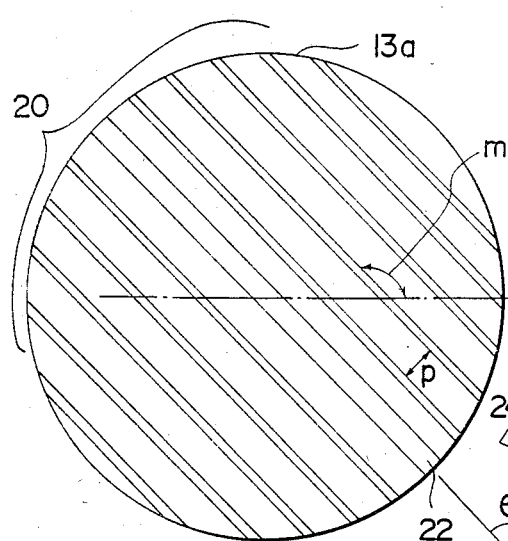
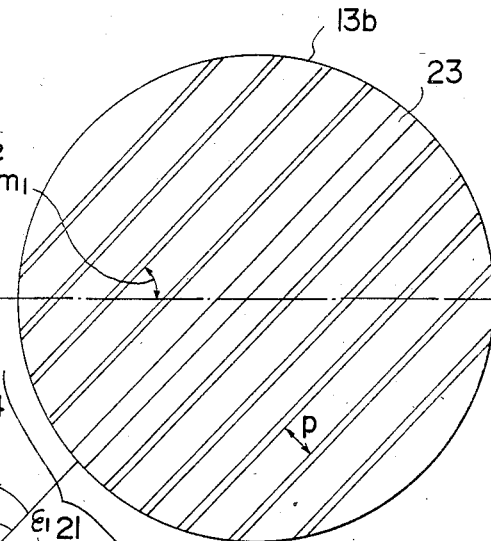
FIG. 16
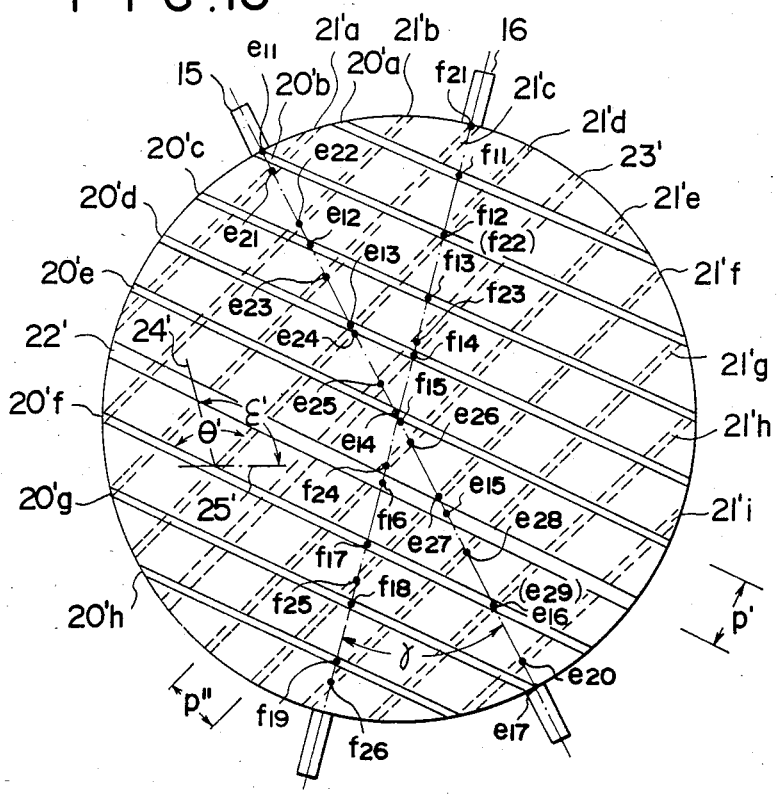

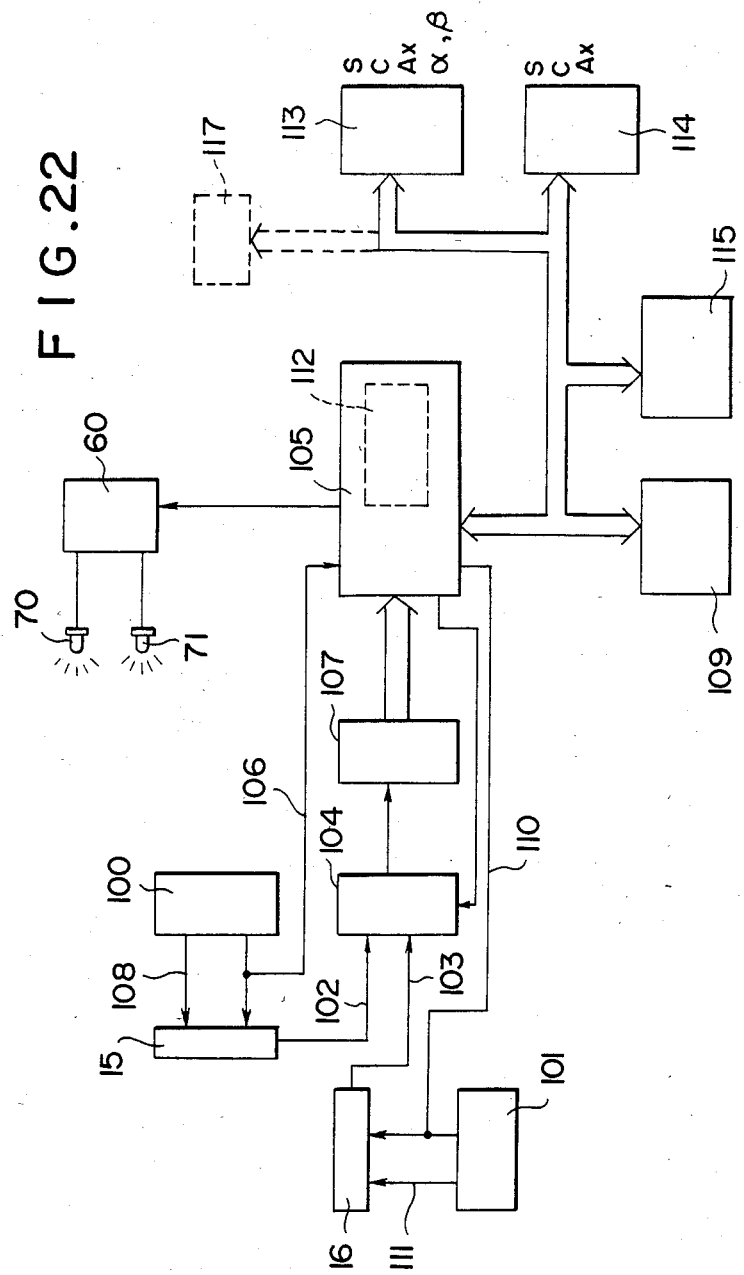

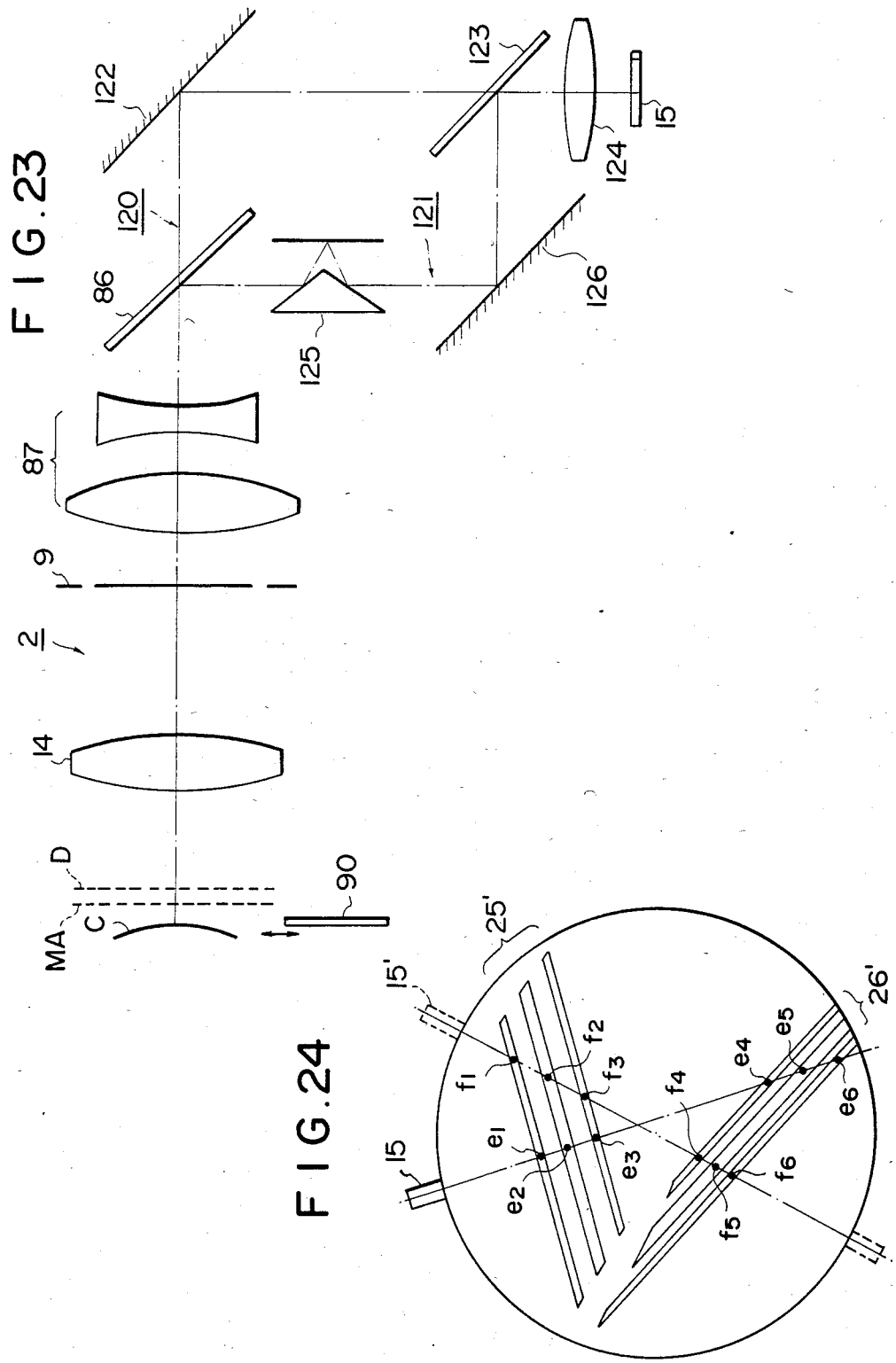

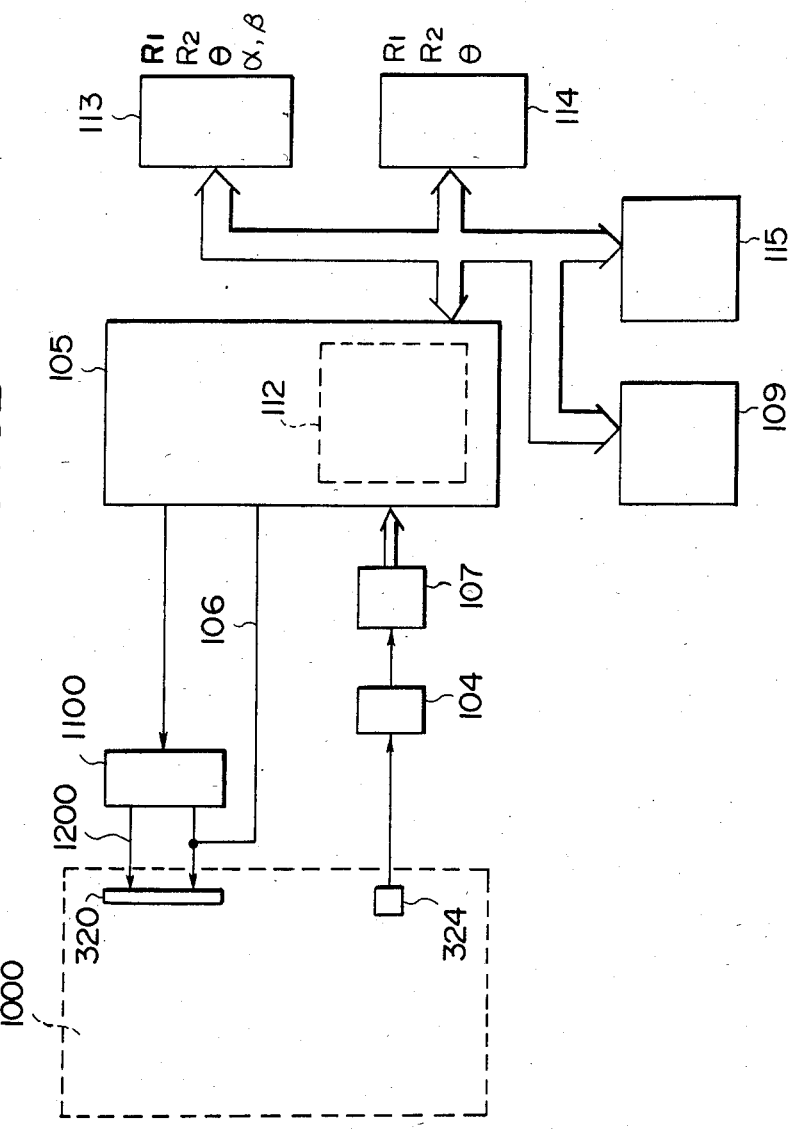

CURVATURE MEASURING APPARATUS

The present invention relates to an apparatus for measuring the radii of curvature of a curved surface and, more particularly, to a curvature measuring apparatus which can be applied to either an ophthalmometer for measuring the radii of curvature of a human cornea or a radius-meter for measuring the radii of curvature of a contact lens.

In the present specification, the principles and embodiments of the present invention will be described mainly in connection with an ophthalmometer. However, the present invention need not be limited to opthalmometers, but could also be generally applied to an apparatus for measuring the radius of curvature of the surface of a curved object which is optically reflective.

The human cornea itself has about 80% of the total refracting power of the whole eye, i.e., about 45 diopters. However, an astigmatic eye has about 75% of the total refracting power, which value is caused by corneal astigmatism, i.e., by the fact that the front face of the cornea is not spherical but toric. When a contact lens is prescribed, its base curve must be prescribed on the basis of the radius of curvature of the front surface of the cornea which is to support the contact lens. From this viewpoint, it is necessary to measure the radius of curvature of the front surface of the cornea. Various types of ophthalmometers have been designed as the apparatus for measuring the radius of curvature of the front surface of the human cornea. These measure the radius of curvature and the astigmatic axes of a cornea from either the changes in size of a projected image or the relative displacement of the reflected image of a visual index partly by projecting one or more visual indices on the cornea to be measured, and partly by observing the size of the projected image or the position of the reflected images of the indices on the focal plane of an observing telescope.

With the ophthalmometer, especially, when measuring an astigmatic cornea having a toric surface, it is necessary to measure three values: the radii of curvature of the first and second principal meridians, and the axial angle of the first principal meridians of the cornea. In order to measure those three values, a conventional ophthalmometer is required to conduct measurements in three steps. However, the human eye is always accompanied by physical vibrations of its ball so that any increase of the measurement time invites vibrations of the projected image due to the vibrations of the eyeball. This results in serious problems such as errors in the measurements or the requirement for frequent alignment adjustments during the measurements.

As apparatus for eliminating the defects concomitant with the prior art apparatus, several have been disclosed such as Japanese Patent Laid-Open No. 56-18837 or 56-66235 or U.S. Pat. No. 4,159,867. In each of these publications, an apparatus is disclosed which defects the reflection of an image projected on a cornea by means of a one- or two-dimensional position sensor thereby measuring the radii of curvature and the axial angle between the principal meridians of the cornea to be measured from that detected position.

However, these apparatus are of the type in which the image reflected from the cornea is focused by means of a telescope in a similar manner as in existing ophthalmometers. As a result, any enhancement of the measurement precision requires an increase of the focal length of the telescope, thus causing the defect that the size of the apparatus is accordingly increased. Because of the focusing method, moreover, a focusing mechanism is required, and the alignment between the apparatus and the cornea to be measured is poor, because it uses a focusing telescope, which means that the time taken by the measurement cannot be reduced, or the process automated. In fact, existing ophthalmometers measure the radii of curvature of the cornea from the size and the displacement of the reflection of an index image projected onto the cornea, which is reflected from the cornea and which is focused in the focal plane of the telescope. Unless the distance between the cornea to be measured and the ophthalmometer, i.e., the operating distance, is maintained precisely therefore, errors directly affect the size or the displacement of the reflected image and, still worse, errors in the measured values accumulate. Therefore, the existing ophthalmometers need consideration of the maintenance of the operating distance and are difficult operate.

An apparatus is disclosed in U.S. Pat. No. 3,880,525 for measuring the refractive characteristics of an optical system, chiefly the spherical or cylindrical refracting power, and the axial angle, of an eyeglass lens. This apparatus is constructed so as to irradiate an eyepiece glass with a parallel beam of light, select the light deflected by the refractive characteristics of the lens using mask means having a point aperture, and project the selected light onto the surface of the image pickup of a plane image detector or a TV camera, which is positioned closer than the focal distance of the lens, so that the refractive characteristics of the lens are determined from the position of the projected point of that light upon said detector, which has passed through the point aperture. However, this U.S. patent disclosed only the measurements of the refractive characteristics of a refracting optical system but has neither disclosed nor hinted at the curvature characteristics of a reflecting optical system, especially the measurements of the radii of curvature of the reflecting curved surface thereof. Since the apparatus detects the refractive characteristics by means of a point aperture, moreover, the detecting means has to use a plane image detector or TV camera so that the apparatus becomes expensive. There arises another defect that if there is dust on the lens being measured, the optical system of the apparatus, or the detection plane, the beam of light as it passes through the point aperture may be obscured by the dust thereby making it impossible to measure the refractive characteristics of that lens.

It is therefore an object of the present invention to provide a curvature measuring apparatus which has succeeded in eliminating the above defects concomitant with prior art ophthalmometers, which can conduct automatic measurements by the use of an afocal optical system and which can be applied to ophthalmometers or radius meters.

A second object of the present invention is to provide a curvature measuring apparatus which can have a smaller size than existing apparatus by using an afocal optical system and which can automatically measure the radii of curvature without the use of such optical elements that make it necessary for a observer to observe or operate it using a focal telescope or the like.

A third object of the present invention is to provide an automatic curvature measuring apparatus which makes it possible to automatically generate such information for the alignment between the curved surface to be measured and the optical axis of the apparatus, which is conducted through collimation by existing apparatus, which is easily operated and which shortens the measurement time.

A fourth object of the present invention is to provide a novel ophthalmometer which is free from any errors in the measured values of the radii of curvature even if the operating distance changes.

A fifth object of the present invention is to provide a curvature measuring apparatus which is resilient against the influences of disturbances, is highly precise and inexpensive, and which is capable of conducting automatic measurements and which makes it possible, by increasing the quantity of information of the mask means, to make use of not only more inexpensive detecting means than that used by existing ophthalmometers, but also an automatic lens meter and to conduct the measurements even if dust is caught in the optical system of the apparatus or on the surface to be measured.

A sixth object of the present invention is to provide an apparatus for measuring radii of curvature, which requires neither the assembly nor adjustment of a position sensor, which has low assembly and adjustment costs, and which is easy to maintain.

In order to achieve these objects, the present invention provides a curvature measuring apparatus comprising: an illuminating optical system for illuminating a surface to be measured, said illuminating optical system including light source means forming a pattern of at least two groups of straight lines in different directions, each being composed of at least two parallel straight lines in a virtual plane, and a collimator lens for orienting the principal ray of an illuminating beam of light emitted from said light source through a pin hole arranged on the optical axis, so that it is parallel to said optical axis; detecting means for detecting the reflection of said illuminating beam of light reflected from said measured surface in a plane which is not optically conjugate with said light source; and arithmetic means for calculating the radii of curvature of said measured surface from the changes in the inclination and pitch of the projected stright-line pattern which is formed by said reflected light detected by said detecting means and which corresponds to said light source.

According to the present invention, moreover, a curvature measuring apparatus is provided comprising: an illuminating light source including a plurality of luminous units arranged in the same virtual plane for irradiating a surface to be measured; optical detecting means positioned in a virtual plane, which is not optically conjugate with the plane in which containing said illuminating light source, which forms a group of straight lines constituting at least two groups of straight lines having different directions of arrangement, each being composed of at least two parallel straight lines; a detecting optical system including an optical element for directing rays of light emitted from said illuminating light source and reflected parallel to the optical axis by said measured surface, toward said optical detecting means through a pin hole which is arranged on said optical axis; and arithmtic means for calculating the radii of curvature of said measured surface from the changes in the inclination and pitch of the straight-line loci which are made by the luminous units of said illuminating light source having emitted rays detected by said optically detecting means.

According to the present invention, still moreover, a curvature measuring apparatus is provided comprising: an illuminating optical system including a light source and collimator means for orienting the rays from said light source into a parallel beam of light; mask means having a straight-line pattern which constitutes at least two groups of straight lines having different directions of arrangement, each being composed of at least two parallel straight lines in a virtual plane so as to select the rays which come from said illuminating optical system and which are reflected by the surface to be measured; detecting means for detecting the reflected rays which have been selected by said mask means; and arithmetic means for calculating the radii of curvature of said detected surface from the changes in the inclination and pitch of the projected straight-line pattern which is detected by said detecting means and which correspond to the straight-line pattern of said reflected rays, wherein said mask means and said detecting means are each arranged in different planes which are not optically conjugate with said light source.

According to the present invention, furthermore, a curvature measuring apparatus is provided comprising: an illuminating light source including a plurality of luminous units; mask means constituting at least two groups of straight lines having different directions of arrangement, each being composed of at least two parallel straight lines in a virtual plane so as to select the rays of light from said illuminating light source; condensing means for introducing those rays of light from said illuminating light source selected by said mask means and reflected by the surface to be measured, which are parallel to the optical axis of said apparatus, into pin-hole means which is arranged on said optical axis; detecting means for detecting the rays which have passed through said pin-hole means; and arithmetic means for calculating the radii of curvature of said measured surface from the changes in the pitch and inclination of the straight-line loci which are made by those luminous units which have emitted rays which were detected by said detecting means, wherein said mask means and said illuminating light source are each arranged in different planes which are not optically conjugate with said pin-hole means.

The apparatus according to the present invention is enabled, by the constructional features thus far described, to have a smaller size, a shorter measurement time, a higher resilience against the influence of disturbances, a higher measurement precision and a lower cost than those of prior art apparatus for measuring radii of curvature, and be able to automatically measure the radii of curvature a curved surface. Since the apparatus of the present invention can automatically generate alignment information, it can achieve shortening of the measurement time and an improvement in the measurement precision. In particular, when the present invention is applied to an ophthalmometer, the advantages thereof can provide an ophthalmometer which is freed from any influence due to the vibrations of the eyeball, which has a high measurement precision, a short measurement time, a small size and a low cost and which can accomplish automatic measurements.

If the present invention is applied to the so-called "radius meter" for measuring either the base curve or the radii of curvature of the front surface of a contact lens, it is possible to provide a radius meter of new type which does not require a optical system, such as a microscope, for observing the target image and for the measurement thereby as is required by existing radius meters, as it is different from radius meters which focus the target image twice, once on the back of the contact lens and once at the center of the curvature of the same thereby measuring the radii of curvature, such as the base curve, from the movement of an objective lens at the same time so that it can conduct such automatic measurements that neither require the diopter adjustment directly governing the measurement precision, nor induce personal errors by the operators, and so that it has a high measurement precision and a short measurement time.

The present invention will be described below with reference to the accompanying drawings in connection with the measurement principles and embodiments in which it is applied to an ophthalmometer for measuring the radii of curvature of a cornea. In the drawings;

FIGS. 1(a) and 2 are perspective views illustrating the first measurement principle of the present invention;

FIG. 1(b) is a plan view of FIG. 1(a);

FIGS. 3(a), (b) and (c) are schematic views illustrating the relationships between the projections of the straight-line light source (or the mask patterns) and the linear sensors implying that the curvature characteristics can be measured by the present invention;

FIG. 6(b) is a plan view of FIG. 6(a);

FIG. 7(b) is a plan view of FIG. 7(a);

FIG. 8 is a view showing the optical arrangement of a first embodiment of the present invention;

FIG. 9 is a view illustrating an example of the aperture pattern on the mask 9;

FIG. 10 is a plan view showing an example of a fixed index;

FIG. 14 is a view showing the optical arrangement of a third embodiment of the present invention;

Figure 18:
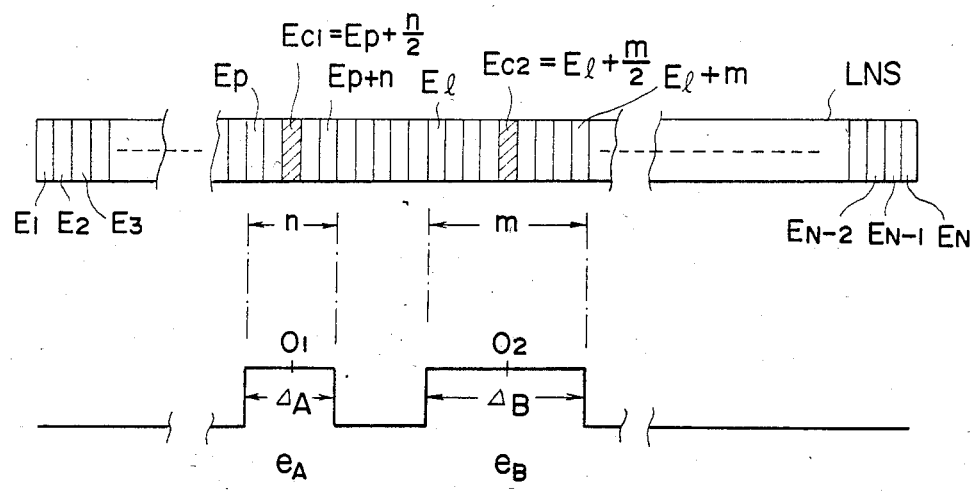
Figure 19:
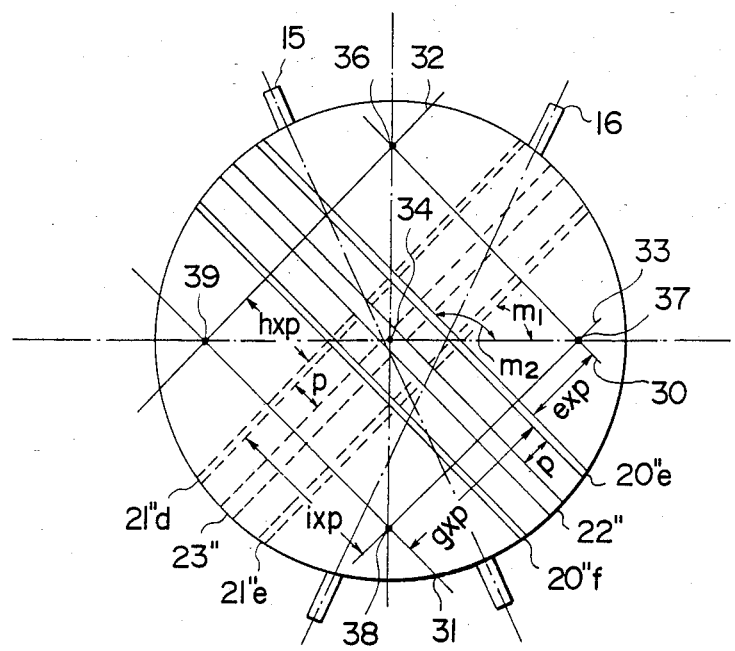
Figure 20:
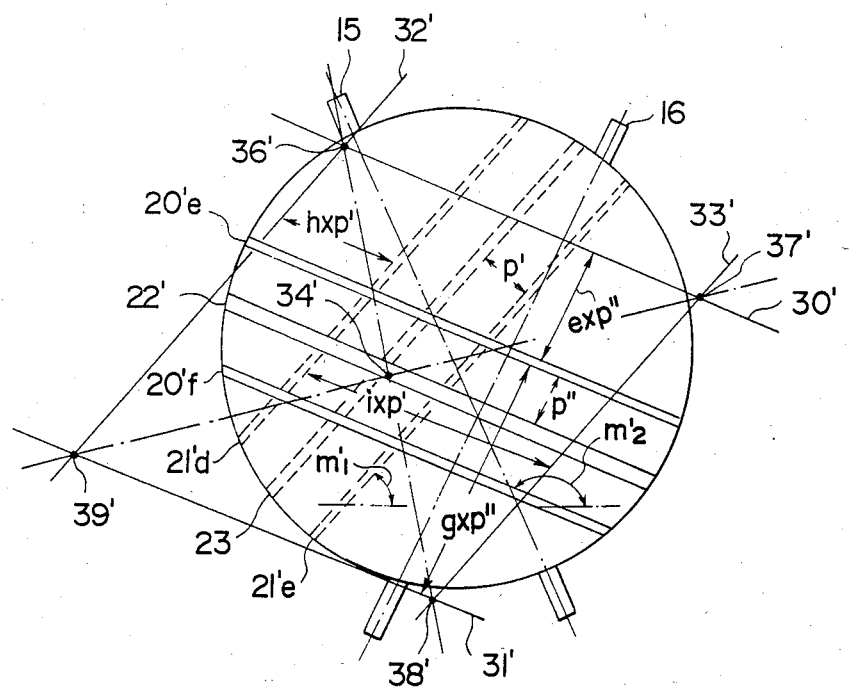
Figure 21:
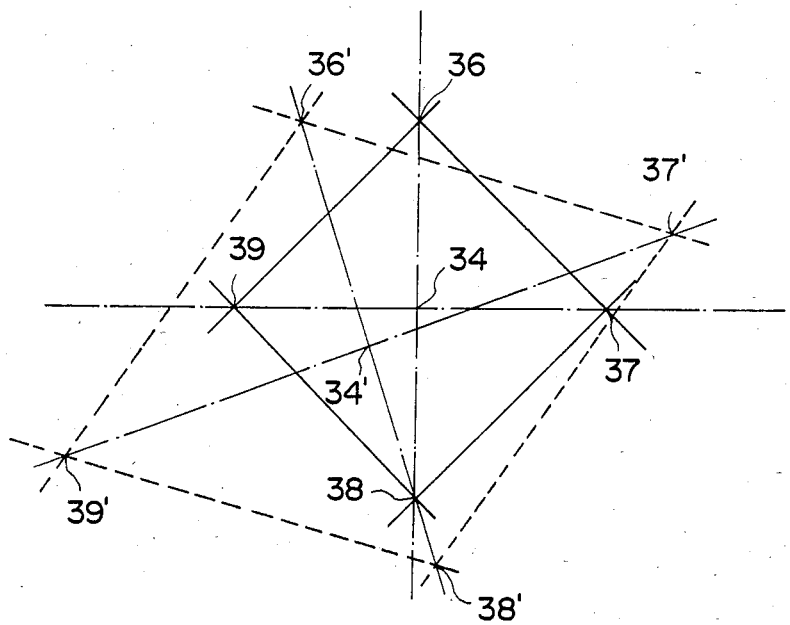
Figure 25:
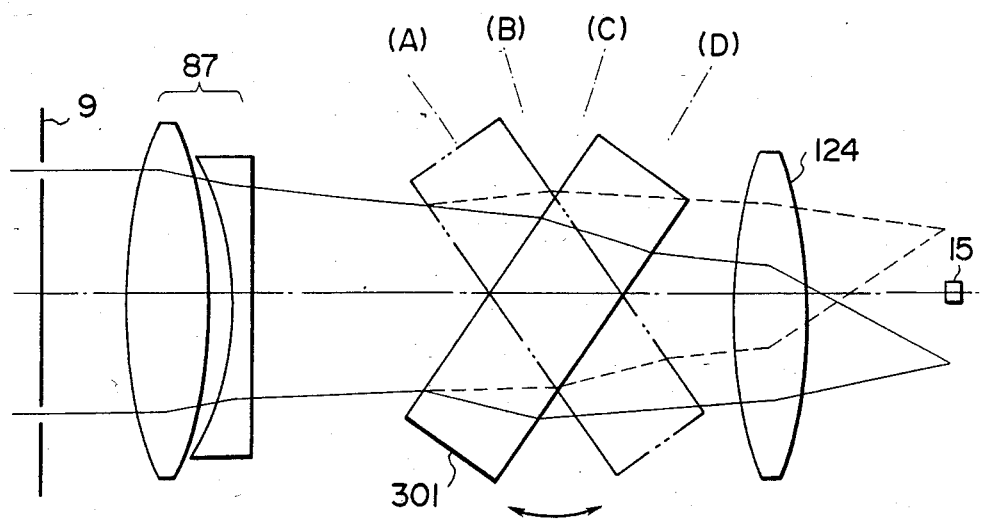
Figure 26:
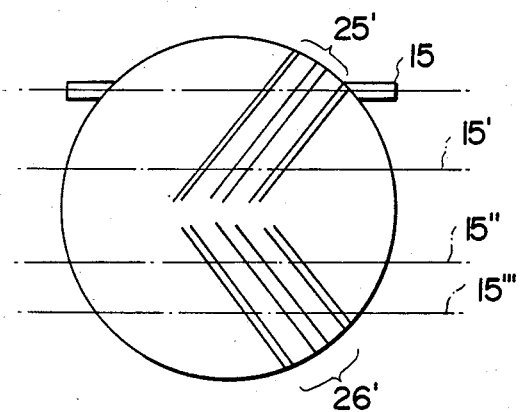
Figure 27:
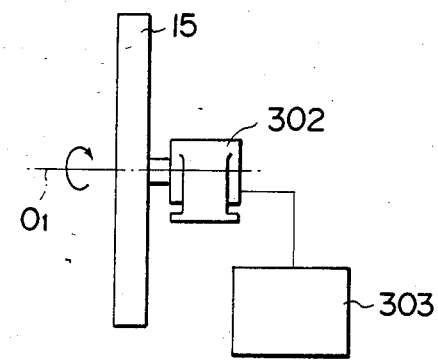
Figure 28:
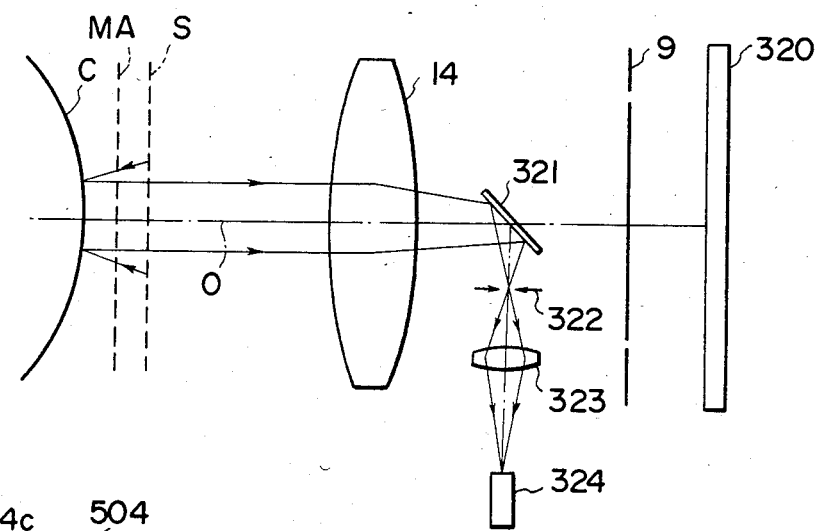
Figure 29:
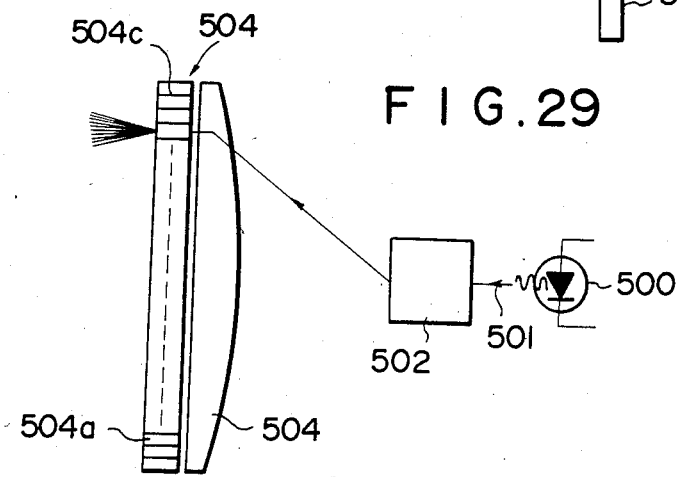
Figure 30:
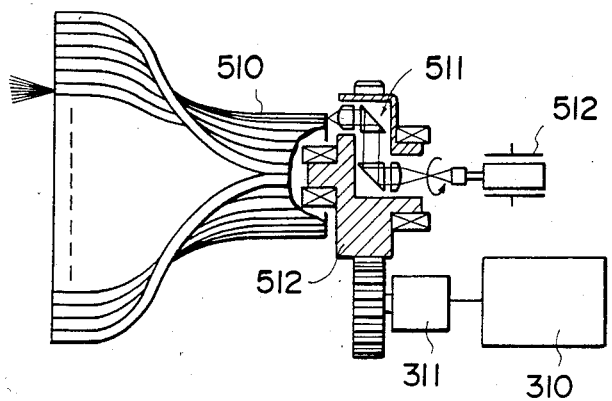
Figure 31:
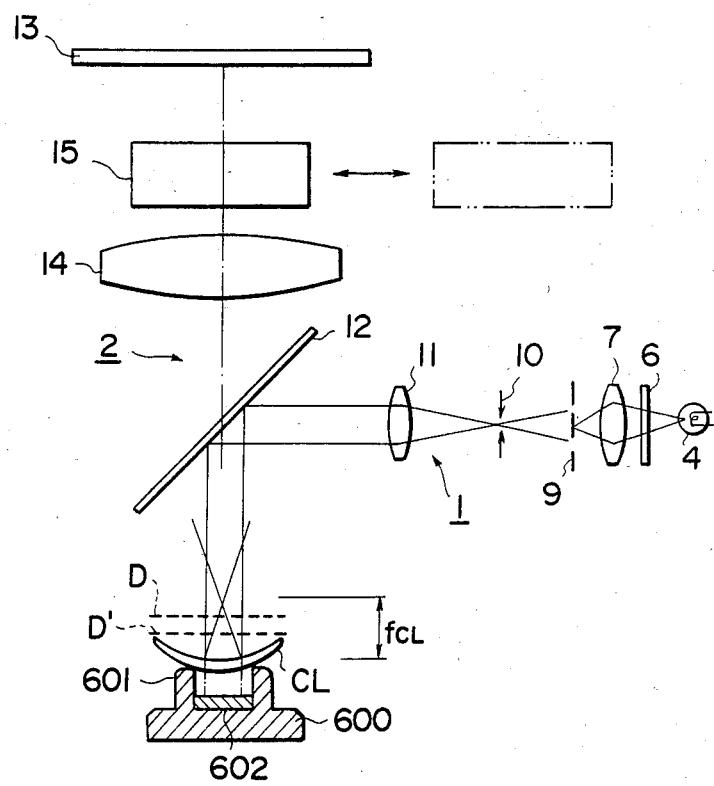

FIGS. 15(a) and (b) are views showing an example of the mask pattern;

FIG. 16 is a schematic view illustrating both the projection of the mask pattern on the linear sensor, and the detected state of the same;

FIGS. 17(A) to (M) are timing charts illustrating the relationships between the outputs detected by the linear sensors and the coordinate values;

FIG. 18 is a view illustrating the arrangement of the elements of the linear sensor explaning the method for determining the coordinate values from the outputs detected by the linear sensors;

FIGS. 19, 20 and 21 are schematic views explaining the measurements based upon the principles of the present invention;

FIG. 22 is a block diagram showing one example of the arithmetic circuit;

FIG. 23 is a view showing the optical arrangement of part of a fourth embodiment of the present invention;

FIG. 24 is a schematic view illustrating both the projections of the mask pattern and the detection of the same by the fourth embodiment;

FIG. 25 is a view showing the optical arrangement of part of a fifth embodiment of the present invention;

FIG. 26 is a schematic view illustrating both the projections and the detections of the mask pattern by the fifth embodiment;

FIG. 27 is a view showing the linear sensor driver of a sixth embodiment;

FIG. 28 is a view showing the optical arrangement of a seventh embodiment of the present invention;

FIGS. 29 and 30 are views illustrating other examples of the luminous element array;

FIG. 31 is a view showing the optical arrangement of an eighth embodiment of the present invention; and FIG. 32 is a block diagram showing one example of the arithmetic circuit of the seventh embodiment.

FIG. 1(a) a perspective view illustrating the first measurement principle of the present invention, and FIG. 1(b) is a plan view of the same.

In these figures, an orthogonal coordinate system $X_0$-$Y_0$ which has its origin at the optical axis $0_1$ of the apparatus is used. It is assumed that a cornea C is so arranged as to have its apex in contact with the plane containing the coordinate system $X_0$-$Y_0$. The cornea C is arranged so as to have its optical center $O_C$ displaced by $E_H$ along the $X_0$-axis and by $E_V$ along the $Y_0$-axis and to have its first principal meridian a with a radius of curvature $R_1$ inclined at an angle $\theta$ with respect to the $X_0$-axis. The second principal meridian of the cornea C is perpendicular with respect to the first principal meridian and is assumed to have a radius of curvature $R_2$. An orthogonal coordinate system $X$ - $Y$ having its origin $O$ on the optical axis $O_1$ of the apparatus is located at a position which is at a distance $l$ away along the optical axis $O_1$ of the apparatus from the $X_0$-$Y_0$ coordinate system, and that the detection plane is the $X$ - $Y$ coordinate plane.

Suppose that rays from a straight-line light source which forms at least two parallel straight-line groups L at pitch P intersecting the $X_0$-axis at an angle m are so focused and projected on the $X_0$-$Y_0$ coordinate plane that the principal rays are parallel to the optical axis $O_1$ of the apparatus. The illuminating rays are deflected and reflected in accordance with the curvature characteristics of the front surface of the cornea C, in other words with the values of the radius of curvature $R_1$ of the first principal meridian, the radius of curvature $R_2$ of the second principal meridian, and the axial angle $\theta$ of the first principal meridian of the cornea C, if the cornea C has a toric surface, until it is directed toward the detection plane D which is so located that it is not optically conjugate with the straight-line light source.

The straight-line pattern L projected on the detection plane D, which corresponds to the straight-line light source, has its pitch and its inclination to the X-axis changed to P' and M, respectively.

If the distance between the detection plane D and the corneal apex $O_C$ is $l$, the inclination of the projected straight-line pattern L' is expressed by the following equation:

$$M = \frac{m[a(l)\sin^2\theta + b(l)\cos^2\theta] + [a(l) - b(l)]\sin\cdot\cos\theta}{m[a(l) - b(l)]\sin\theta\cdot\cos\theta] + [a(l)\cos^2\theta + b(l)\sin^2\theta]} \quad (1)$$

The change in pitch P' is expressed by the following equation:

$$\frac{P'}{P} = a^2(l)\sin^2\theta + b^2(l)\cos^2\theta + \frac{a^2(l) - b^2(l)}{m^2 + 1}[\cos^2\theta + m\sin^2\theta] \quad (2)$$

Here, both equations (1) and (2) can be written in the following forms:

$$\left.\begin{array}{l} a(l) = 1 + \dfrac{2l}{R_1} \\ b(l) = 1 + \dfrac{2l}{R_2} \end{array}\right\}$$

Figure 2:
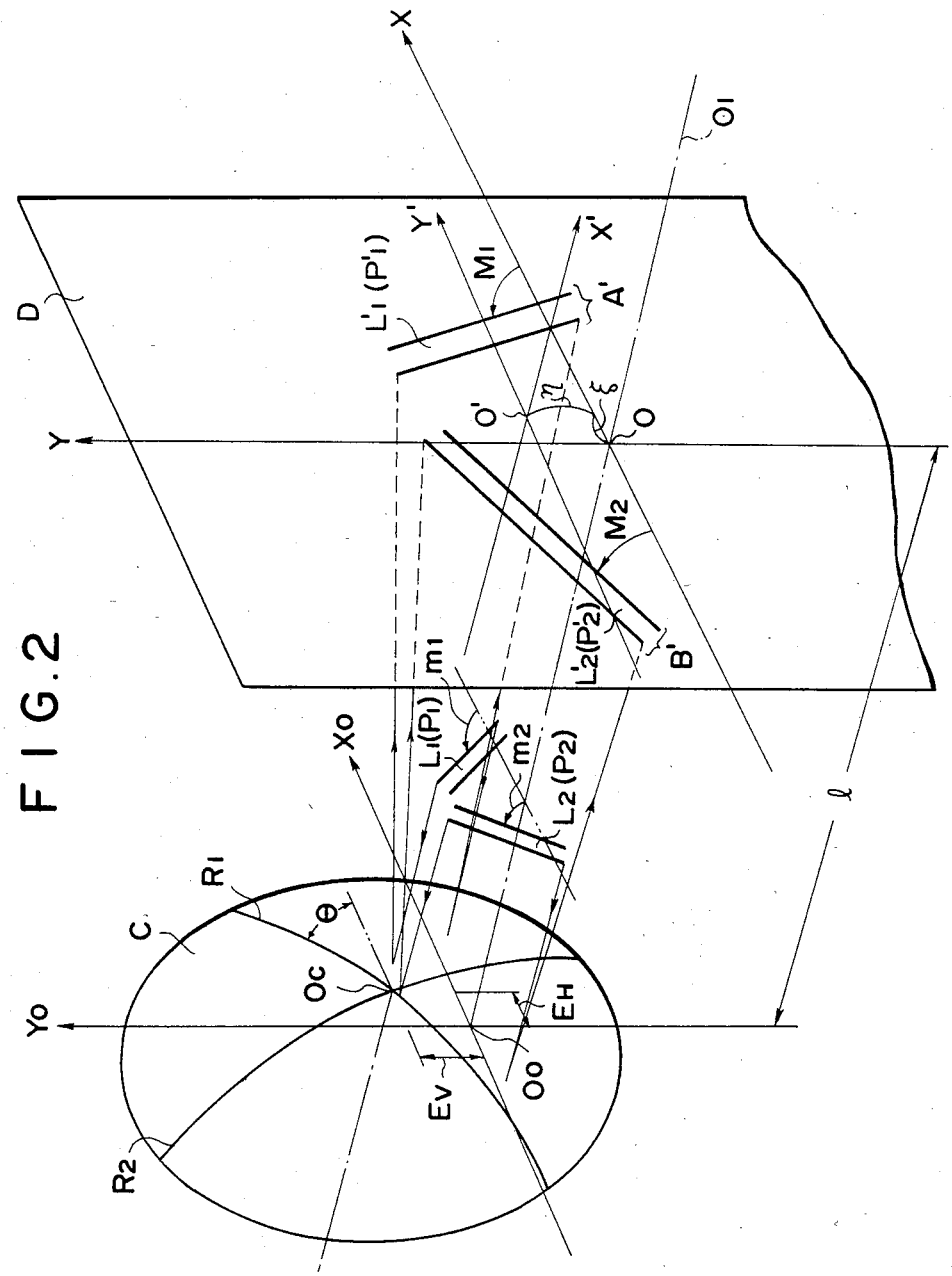

Upon practical measurement, the facial shape characteristics of the cornea C can be measured from the changes in the inclination and pitch of the parallel straight-line groups in accordance with equations (1) and (2). Since these equations (1) and (2) have three unknowns $R_1$, $R_2$ and $\theta$, it is understood that they cannot be solved only by the change of one parallel straight-line group. It is therefore necessary in practice to know the changes in the inclination and pitch of a second parallel straight-line groups in addition to those of the first parallel straight-line group. This construction is illustrated in FIG. 2. As shown in FIG. 2, a straight-line light source is arranged which constitutes both a group $L_1$ of two parallel straight lines having an inclination $m_1$ and pitch $P_1$ and a group $L_2$ of two parallel straight lines having an inclination $m_2$ and pitch $P_2$. The rays of light emitted from the light source and reflected by the cornea C forms a group $L_1'$ of two projected parallel straight lines having an inclination $M_1$ and a pitch $P_1'$, and a group $L_2'$ of two projected parallel straight lines having an inclination $M_2$ and a pitch $P_2'$ on the detection plane D. Since two sets of equations (1) and (2), i.e., four equations, are obtained from those two sets of projected parallel straight-line groups, the unknowns $\theta$, $R_1$ and $R_2$ of equations (1) and (2) can be determined. If the arithmetical determinations of $R_1$, $R_2$ and $\theta$ by solving the quadratic equations (1) and (2) are so complicated as to increase the cost of the calculating mechanism and the length of the processing time, it is sufficient to execute the following intermediate calculations.

Figure 3A:
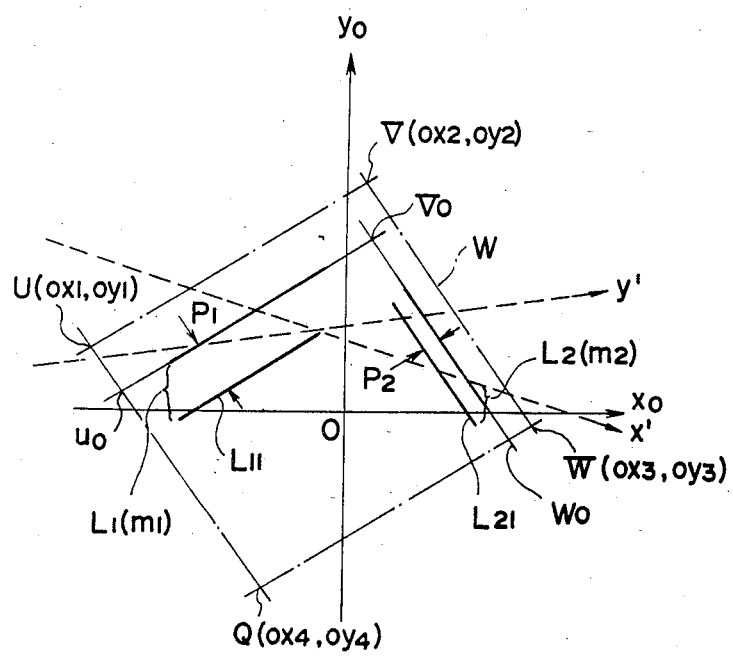

FIG. 3a illustrates the parallel straightline groups $L_1$ and $L_2$ which are formed by the straightline light source of FIG. 2. It is similar to FIG. 2 in that the group $L_1$ has a inclination $m_1$ and pitch $P_1$, and the group $L_2$ has a inclination $m_2$ and pitch $P_2$. Suppose that there is a parallel line $\overline{UV}$ at a distance $eP_1$, which is e times as long as the pitch $P_1$, and a parallel line $\overline{QW}$ at a distance $fP_1$, which is f times as long as the pitch $P_1$, from one $L_{11}$ of the parallel straight lines $L_1$.

Figure 3B:
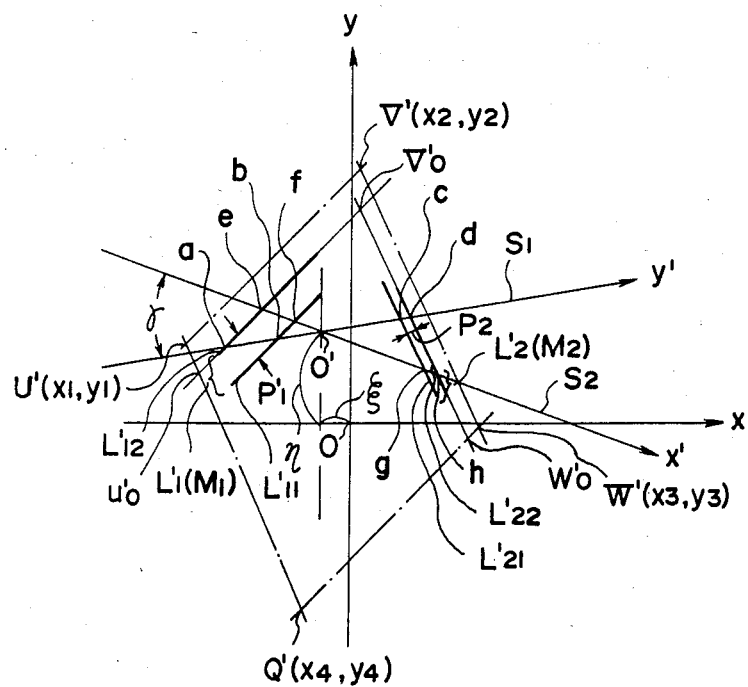

In addition, suppose that there are two parallel lines $\overline{VW}$ and $\overline{UQ}$ at distances $gP_2$ and $hP_2$, respectively, from one $L_{21}$ of the parallel lines $L_2$. These lines $\overline{UV}$, $\overline{QW}$, $\overline{VW}$ and $\overline{UQ}$ form a reference imaginary parallelogram UVWQ, the four apexes of which have the virtual coordinates $U(_0x_1, _0y_1)$, $V(_0x_2, _0y_2)$, $W(_0x_3, _0y_3)$ and $Q(_0x_4, _0y_4)$ in the $x_0$-$y_0$ coordinate system FIG. 3b is a diagram illustrating the projected parallel straight-line groups $L_1'$ and $L_2'$ which are formed by reflecting the parallel straight-line groups $L_1$ and $L_2$ of FIG. 3a from the cornea C and by projecting them onto the detection plane D. It is similar to FIG. 2 in that the group $L_1'$ has its inclination and pitch changed to $M_1$ and $P_2'$, respectively, whereas the group $L_2'$ has its inclination and pitch changed to $M_2$ and $P_2'$, respectively. The projected parallel straight-line groups may be detected by means of a plane position sensor which is arranged in the detection plane D. However, if those groups are detected by means of linear position sensors $S_1$ and $S_2$ that intersect at an angle of intersection $\gamma$ at a point O' which is shifted by $\xi$ along the X-axis and by $\eta$ along the Y-axis from the origin 0 in the X - Y coordinates, the linear position sensor $S_1$ detects the projected parallel straight-line groups at points a, b, c and d whereas the linear position sensor $S_2$ detects the projected parallel straight-line groups at points e, f, g and h. The equation of one of the projected parallel straight-line groups $L_{11}'$ is extracted from the detection points b and f, and the equation of another group $L_{21}'$ is extracted from the detection points c and g. Likewise, the equation of the projected parallel straight-line group $L_{12}'$ can be extracted from the detection points a and e whereas the equation of group $L_{22}'$ can be extracted from the detection points d and h so that not only the pitch $P_1'$ of the groups $L_{11}'$ and $L_{12}'$ but also the pitch $P_2'$ of the groups $L_{21}'$ and $L_{22}'$ can be calculated. It is also possible to suppose a parallel line U'V' at a distance $eP_1'$, which is e times as long as the pitch $P_1$, as illustrated in FIG. 3a from the group $L_{11}'$. Likewise, a parallel line Q'W' at a distance fP' from the group $L_{11}'$ can also be supposed. It is also possible to suppose parallel lines $\overline{V'W'}$ and $\overline{U'Q'}$ at distances $gP_2'$ and $hP_2'$, respectively, from the group $L_{21}'$. These parallel lines $\overline{U'V'}$, $\overline{Q'W'}$, $\overline{V'W'}$ and $\overline{U'Q'}$ generate a first projected virtual parallelogram U'V'W'Q'. If this virtual parallelogram has its four apexes located at $U'(x_1, y_1)$, $V'(x_2, y_2)$, $W'(x_3, y_3)$ and $Q'(x_4, y_4)$ in the virtual coordinates of the X - Y coordinate system, the reference virtual parallelogram UVWQ of FIG. 3a and the first projected virtual parallelogram U'V'W'Q' correspond to each other. This particular transformation relates to the curvature characteristics of the cornea being measured.

The following coefficients and equations will be defined for the four virtual points:

$$\left.\begin{array}{l} A_{ij} = (_0x_i - x_i) - (_0x_j - x_j) \\ A_{ik} = (_0x_i - x_i) - (_0x_k - x_k) \\ B_{ij} = (_0y_i - y_i) - (_0y_j - y_j) \\ B_{ik} = (_0y_i - y_i) - (_0y_k - y_k) \\ C_{ij} = _0x_i - _0x_j \\ C_{ik} = _0x_i - _0x_k \\ D_{ij} = _0y_i - _0y_j \\ D_{ik} = _0y_i - _0y_k \end{array}\right\} \quad (3a)$$

Here the letters i, j and k are assumed to take j and k by using i as a reference. Twelve combinations can be made from the four virtual points.

If the equations (3a) are used, the values $R_1$ and $R_2$ of the radii of the two principal meridians can be expressed by the following quadratic equation:

$$4(C_{ik}D_{ij} - C_{ij}D_{ik})(l/R)^2 - 2(A_{ij}D_{ik} + B_{ik}C_{ij} - A_{ik}D_{ij} - B_{ij}C_{ik})(l/R) + (A_{ik}B_{ij} - A_{ij}B_{ik}) = 0 \quad (3b)$$

The following parenthetic equations of the above coefficients will be defined:

$$[p, q] = p_{ij}q_{ik} - q_{ij}p_{ik}$$

$$[p, q] = -[q, p]$$

If the letters p and q take one of values A, B, C and D, the equation (3b) is expressed in the following form:

$$4[C, D](l/R)^2 - \{[B, C] - [A, D]\}(l/R) + [A, B] = 0 \quad (3c)$$

l is the distance between the cornea C and the detection plane D, as shown in FIG. 2.

Hence, the quadratic equation (3c) can be solved to give the roots $\lambda_1$ and $\lambda_2$ from the four apexes of the first projected virtual parallelogram, shown in FIG. 3b, by detecting the pitches $P_1'$ and $P_2'$ and the inclinations $M_1$ and $M_2$ of the two projected groups of parallel straight lines $L_1'$ and $L_2'$ shown in FIG. 2:

$$\lambda_1 = 1/R_1, \; \lambda_2 = 1/R_2 \quad (4a)$$

Figure 3C:
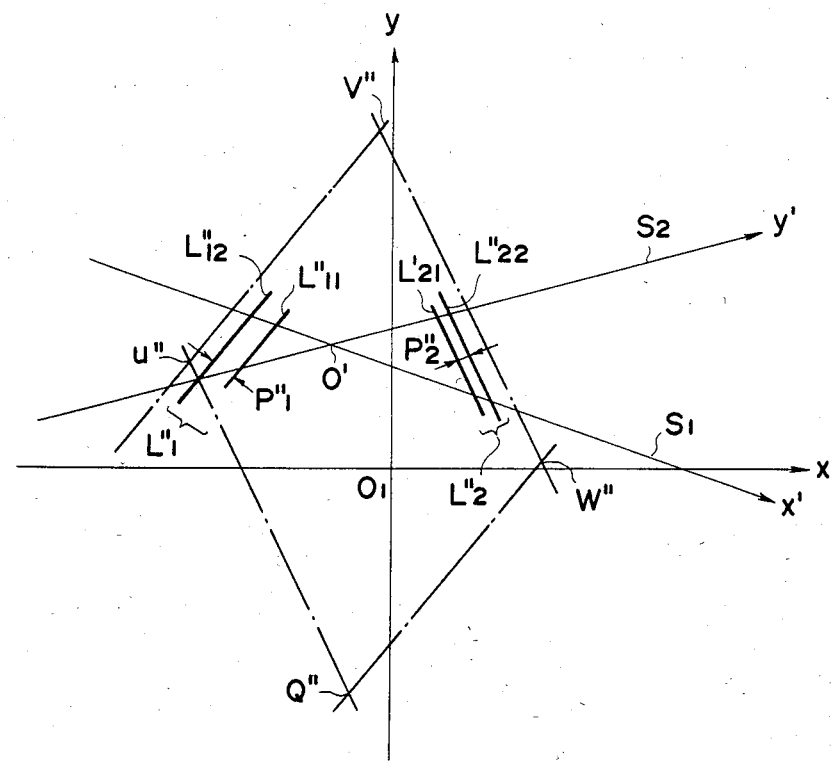

The detection plane D is shifted to a position at a distance l, from the cornea C thereby forming a detection plane D', as illustrated in FIG. 1(b), the above equations (3a) to (3c) can also be applied to the second projected virtual parallelogram, as illustrated in FIG. 3c which is generated by the projected parallel straight-line groups $L_1''$ and $L_2''$ in the detection plane D'. If the two roots of the equations (3a) to (3c) are designated as $\lambda_1'$, and $\lambda_2'$, they are expressed by the following equations:

$$\lambda_1' = l'/R_1', \; \lambda_2' = l'/R_2 \quad (4b)$$

From these equation (4b) and equation (4a), the following equations can be obtained:

$$R_1 = \frac{\lambda_1 - \lambda_1'}{l - l'} \quad (4c)$$

$$R_2 = \frac{\lambda_2 - \lambda_2'}{l - l'}$$

These equations imply that, if the detections are conducted at two planes D and D', the measurement results do not depend upon the operating distance, i.e., the distance $\epsilon$ between the reference plane P of the apparatus and the apex $O_C$ of the cornea C, as illustrated in FIG. 1b, according to the present measurement principle. It is, therefore, unnecessary to conduct the measurements by precisely setting the operating distance, which makes it different from the prior art ophthalmometers, which is a major advantage of the present measurement principle. The angle of the first principal meridian makes with the $X_0$-axis can be determined from the following equation:

$$\theta = \frac{1}{2} \tan^{-1}\left(\frac{[B, D] - [A, C]}{[A, D] + [B, C]}\right) + 90° \quad (5)$$

In FIGS. 3a, 3b and 3c, the pitches $P_1$, $P_2$, $P_1'$, $P_2'$, $P_1''$ and $P_2''$ have been multiplied by the corresponding arbitrary factors e, f, g and h so as to determine the virtual parallelograms. As a matter of fact, however, the operations can be simplified further if the calculations are conducted by making use of the virtual parallelograms $U_0V_0W_0Q$ and $U_0'V_0'W_0'Q$ with e=1 and g=1.

Figure 4:
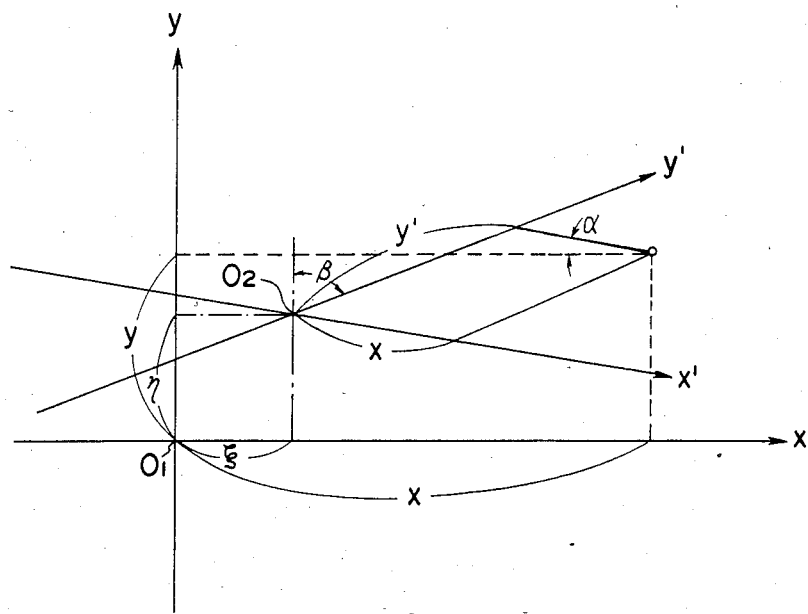
FIG. 4 illustrates the relationship between the orthogonal coordinate system and the oblique coordinate system.

The coordinates of the apexes of the virtual parallelograms have been explained by making use of the $x_0$- $y_0$ orthogonal coordinate system and the X - Y orthogonal coordinate system. However, if an oblique coordinate system X' - Y' is supposed along the directions of the linear sensors $S_1$ and $S_2$, a coordinate transformation between the X - Y orthodinale coordinate system and the X' - Y' oblique coordinate system is made, as illustrated in FIG. 4, such that the X axis and the X' axis intersect at an angle $\alpha$ and the Y axis and the Y' axis intersect at angle $\beta$, and the X' - Y' coordinate system has its origin $O_2$ shifted by $\xi$ along the X-axis and by $\eta$ along the Y-axis from the origin $O_1$ of the X - Y coordinate system. The transformation from the X' - Y' coordinate system to the X - Y coordinate system is expressed by the following equations:

$$\left. \begin{array}{l} X = X' \sin\alpha + Y' \sin\beta + \xi \\ Y = Y' \cos\beta - X' \cos\alpha + \eta \end{array} \right\} \quad (6)$$

From equation (3), the following equation is extracted:

$$A_{ij} = ({}_0x_i - x_i) - ({}_0x_j - x_j)$$

Substitution of equation (6) into the above equation will produce the following equation:

$$\begin{aligned}
A_{ij} &= \{({}_0x_i' \sin\alpha + {}_0y_i' \sin\beta + \xi) - \\
&\quad (x_i' \sin\alpha + y_i' \sin\beta + \xi)\} - \{({}_0x_j' \sin\alpha + \\
&\quad {}_0y_j' \sin\beta + \xi) - x_j' \sin\alpha - y_j' \sin\beta + \xi)\} \\
&= \sin\alpha\{({}_0x_i' - x_i') - ({}_0x_j' - x_j')\} + \\
&\qquad\qquad \sin\beta\{({}_0y_i' - y_i') - ({}_0y_j' - y_j')\} \\
&= A_{ij}' \sin\alpha + B_{ij}' \sin\beta
\end{aligned} \quad (7a)$$

By calculations similar to the above for $B_{ij} = ({}_0y_i - y_i) - ({}_0y_j - y_j)$, moreover, the following equation is obtained:

$$\begin{aligned}
B_{ij} &= \cos\beta\{({}_0y_i' - y_i') - ({}_0y_j' - y_j')\} - \\
&\qquad\qquad \cos\alpha\{({}_0x_i' - x_i') - ({}_0x_j' - x_j')\} \\
&= B_{ij}' \cos\beta - A_{ij}' \cos\alpha
\end{aligned} \quad (7b)$$

Likewise:

$$C_{ij} = C'_{ij} \sin\alpha + D'_{ij} \sin\beta \quad (7c);$$

and $$D_{ij} = D'_{ij} \cos\beta - C'_{ij} \cos\alpha \quad (7d)$$

Here, [C, D], [B, C], [A, D] and [A, B] are extracted from equations (7a) to (7d) in the following:

$$\begin{aligned}
[C, D] &= C_{ij}D_{ik} - D_{ij}C_{ik} \\
&= (C_{ij}' \sin\alpha + D_{ij}' \sin\beta)(D_{ik}'\cos\beta - \\
&\qquad C_{ik}' \cos\alpha) - (D_{ij}' \cos\beta - \\
&\qquad\qquad C_{ij}' \cos\alpha)(C_{ik}' \sin\alpha + D_{ik}' \sin\beta) \\
&= (\sin\alpha \sin\beta + \cos\alpha \sin\beta)[C, D']
\end{aligned}$$

Likewise:
$$[B, C] = (\sin\alpha \sin\beta + \sin\beta \cos\alpha)[A', B']$$
$$\begin{aligned}{}[A, D] &= \sin\alpha \cos\beta[A', D'] - \\
&\quad \sin\alpha \cos\alpha[A', C'] + \sin\beta \cos\beta[B', D'] - \\
&\qquad\qquad \sin\beta \cos\alpha[B', C']
\end{aligned}$$
$$[A, B] = (\sin\alpha \cos\beta + \cos\alpha \sin\beta)[A', B']$$
Moreover:
$$[B, C] - [A, D] = (\sin\alpha \cos\beta + \cos\alpha \sin\beta)\{[B', C'] - [A', D']\}$$

Therefore, equation (3c) is expressed in the following form:

$$\sin(\alpha + \beta) \times \left\{ 4[C', D'] \left(\frac{l}{R}\right)^2 - 2([B', C'] - [A', D']) \left(\frac{l}{R}\right) + [A', B'] \right\} = 0$$

The parenthetized terms {} become a quadratic equation which has the same form as that of equation (3c). From this, it can be understood that the quadratic equation (3c) is such an invariant equation that it has no relationship with the coordinate system selected. This implies that the two linear sensors acting as the detectors can enjoy many degrees of freedom in their arrangements. In other words, the two linear sensors need not be placed in the X - Y coordinate system and on the orthogonal coordinate axes, as is different from the prior art, but may be placed in the X' - Y' coordinate system. Therefore, those arrangements can be made to have no relationship with the measurement precision even if no consideration is taken of the orthogonal precision and the optical axis alignment of the linear sensors. During the measurements, moreover, the parallel straight-line patterns $L_1'$ and $L_2'$ in the conjugate detection plane D are detected in advance by means of the linear sensors $S_1$ and $S_2$ which are arranged on the X'- and Y'-axes of the oblique coordinate system X' - Y'. The virtual parallelogram U'V'W'Q' generated by these detections are used as the first projected virtual parallelogram. Then a shift is made to the conjugate detection plane D' thereby generating the second projected virtual parallelogram U''V''W''Q''. The curvature characteristics of the cornea being measured are determined from the first and second projected virtual parallelograms. These two parallelograms consider their coordinate system only for the X' - Y' coordinate system of the oblique coordinate system X' - Y' which can be selected as required. At the same time, this oblique coordinate system X' - Y' selected is such an invariant for the quadratic equation for calculating the radii of curvature for the curvature characteristics of the cornea being measured. According to the present invention, a remarkably advantageous effect can be attained that no adjustment in the assembly and maintenance is required for the arrangements of the linear sensors $S_1$ and $S_2$.

The axial angle of the cornea is given by equation (5), which corresponds to the orthogonal coordinate system. When the sensors are placed in the oblique coordinate system X' - Y', the results obtained for the oblique coordinate system by the use of the following equation can be calculated in the axial direction when the orthogonal coordinate system is used:

$$\theta = \frac{1}{2} \tan^{-1}$$

$$\times \left( \frac{\cos 2\beta [B',D'] - \cos(\alpha - \beta) \cdot ([A',D'] \div [B',C']) + \cos 2\alpha [A',C']}{\sin 2\alpha [B',D'] + \sin(\alpha - \beta)([A',D'] \div [B',C']) - \sin 2\alpha [A',C']} \right)$$

Figure 5:
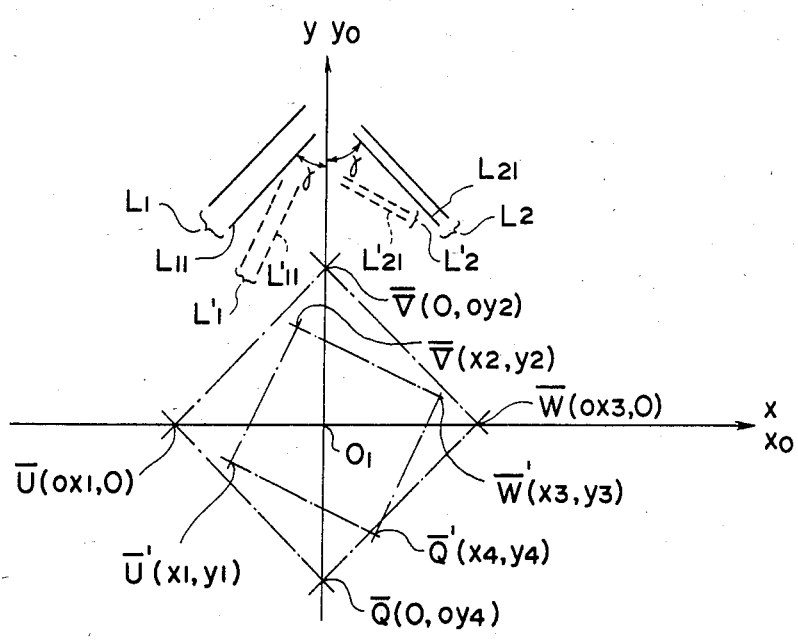
FIG. 5 is a view illustrating the relationship between the straight-line light source (or the mask pattern) and the virtual parallelogram.

Next, the measurement principles of the displacements (which will be referred to as "alignments") of the apex of the cornea and the apparatus optical axis $O_1$ in the vertical and horizontal directions will be described with reference to FIG. 5.

In the calculations of the alignment values by the $X_0 - Y_0$ and X - Y orthogonal coordinate systems, a straight line $\overline{UV}$ is drawn at a distance $e'P_1$ from one of the straight lines $L_{11}$ or $L_{21}$ of the parallel straight-line groups $L_1$ or $L_2$ having pitches $P_1$ and $P_2$, respectively, which are arranged symmetrically at equal angles to the $Y_0$-axis, and straight lines $\overline{WQ}$, $\overline{VW}$ and $\overline{UQ}$ at distances $f'P_1$, $g'P_2$ and $h'P_2$, respectively, are so similarly drawn that the four apexes of the virtual parallelogram $\overline{UVWQ}$ are located on the $X_0$ and $Y_0$ axes. In other words, the center of the virtual parallelogram is located on the measurement optical axis 0 if the virtual parallelogram is generated symmetrically about the measurement optical axis $O_1$. Next, the cornea being measured is measured to detect the projected parallel straight-line groups $L_1'$ and $L_2'$, and a straight line $\overline{U'V'}$ at a distance $e'P_1'$ from the projected parallel straight line $L_{11}'$ is drawn. Likewise, straight lines $\overline{W'Q'}$, $\overline{V'W'}$ and $\overline{U'Q'}$ at distances $f'P_1'$, $g'P_2'$ and $h'P_2'$, respectively, are drawn to generate the first projected virtual parallelogram $\overline{U'V'W'Q'}$. This first projected virtual parallelogram has its four apexes located at $\overline{U'}(x_1, y_1)$, $\overline{V'}(x_2, y_2)$, $\overline{W'}(x_3, y_3)$ and $\overline{Q'}(x_4, y_4)$ in the X - Y coordinate system. From the coordinates of those four apexes, the horizontal alignment $\alpha$ and the vertical alignment $\beta$ are expressed by the following equations:

$$\alpha = \frac{\sum_{i}^{4} x_i}{4} \qquad (10)$$

$$\beta = \frac{\sum_{i}^{4} y_i}{4}$$

When the measurements are conducted in the oblique coordinate system X' - Y', it is sufficient that the initial virtual points are located at $(_0x_1, _0y_1)$, $(_0x_2, _0y_2)$, $(_0x_3, _0y_3)$ and $(_0x_4, _0y_4)$ on the basis of symmetry similarly to the case of the orthogonal coordinate system, and to set the virtual points in a manner to satisfy the following equations:

$$\begin{cases} _0x_1 + _0x_2 + _0x_3 + _0x_4 = 0 \\ _0y_1 + _0y_2 + _0y_3 + _0y_4 = \end{cases} \qquad (12)$$

Since the horizontal and vertical alignments $\alpha$ and $\beta$ are given by equation (10), moreover, equation (12) is transformed by equation (6) into the following forms:

$$\left. \begin{array}{l} \sum_{i}^{4} _0x_i' \sin\alpha + \sum_{i}^{4} _0y_i' \sin\beta + 4\xi = 0 \\ \sum_{i}^{4} _0y_i' \cos\beta - \sum_{i}^{4} _0x_i' \cos\alpha + 4\eta = 0 \\ \phantom{\sum_{i}^{4}} (9) \end{array} \right\} \qquad (13)$$

If equation (10) is similarly transformed by equation (6), the following equations are obtained:

$$4\alpha = \sum_i^4 x_i' = \sum_i^4 x_i' \sin\alpha + \sum_i^4 y_i' \sin\beta + 4\xi$$
$$4\beta = \sum_i^4 y_i' = \sum_i^4 y_i' \cos\beta - \sum_i^4 x_i' \cos\alpha + 4\eta$$

(14)

The alignments are the differences between the coordinates ($_0x_i'$, $_0y_i'$) of the initial virtual point ($_0x_i$, $_0y_i$) in the oblique coordinate system, when the cornea is not being measured, and the coordinates ($x_i'$, $y_i'$) in the oblique coordinate system when the cornea being measured is in the measuring system. Therefore, the following equations are obtained from equations (13) and (14):

$$\begin{cases} \alpha = \dfrac{\sin\alpha \sum_i^4 (x_i' - {_0x_i'}) + \sin\beta \sum_i^4 (y_i' - {_0y_i'})}{4} \\ \beta = \dfrac{\cos\beta \sum_i^4 (y_i' - {_0y_i'}) - \cos\alpha \sum_i^4 (x_i' - {_0x_i})}{4} \end{cases}$$

(15)

These equations express those alignments.

In the present measurement principle thus far described, the measurements of the radii of curvature of the cornea can be calculated by the use of invariant equations which have no relationship with the selection of the coordinate system. For the axial alignment, however, an oblique-orthogonal coordinate transformation is required to transform equations (12) and (15). In spite of this, if the calculation is complicated, it is sufficient to transform the measured coordinates (x', y') in the oblique coordinate system into orthogonal coordinates by the use of equation (6) and to subsequently calculate the axial alignment by the use of equations (5) and (10) in the orthogonal coordinate system.

Thus, according to the present invention, if a virtual parallelogram which is symmetrical about the optical axis O is prepared from the parallel straight-line groups $L_1$ and $L_2$ of the light source when the cornea being measured is not in the measurement optical path, the alignment can be calculated by subsequently placing the cornea into the measuring optical system thereby producing a similar projected virtual parallelogram from the projected parallel straight-line image. Using those calculations, the measurements can be conducted independently without any knowledge of the radii of curvature of the first and second principal meridians and the angle of inclination of then to the cornea. This is remarkably advantageous over prior art ophthalmometers if consideration is taken into the points that no prior art ophthalmometer has succeeded in numerically calculating the alignment, and that the cornea being measured is aligned with the center of the cross of a reticle plate while being observed by means of a measuring telescope. Moreover, since the calculation steps of both the curvature characteristics and the alignment of the cornea can be advanced independently of and simultaneously with each other as numerical calculations, automatic alignment can be made while shortening the arithmetic time if the alignment quantities are electrically fed to an apparatus traversing system.

Figure 3D:
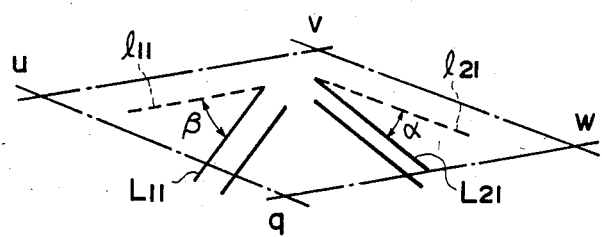

The virtual parallelogram is generated by multiplying the pitches of the straight-line groups, to which the straight lines $L_{11}$ and $L_{21}$ belong, by multipliers, and by drawing virtual straight lines parallel to the inclinations of the straight lines $L_{11}$ and $L_{21}$. However, the method of generating the virtual parallelogram should not be limited to the above method but could be executed in such a way that a virtual straight line $l_{11}$ at an angle of $\beta$ to the straight line $L_{11}$, and a virtual straight line $l_{21}$ at an angle of $\alpha$ to the straight line $L_{21}$ are drawn, as illustrated in FIG. 3d, to generate a virtual parallelogram uvwq on the basis of the virtual straight lines $l_{11}$ and $l_{21}$ thus generated. By this particular method, the measurement principle of the present invention should not be changed in the least.

The "principle of reciprocity of rays" can be applied to the first principle thus far described. As illustrated in FIG. 2, more specifically, a planar luminous element, which has a plurality of luminous units arranged in a planar form, is placed in the detection plane D, and light-receiving means, which has straight light-receiving units with the same arrangement, is placed at the positions of the straight-line light sources $L_1$ and $L_2$. Straight lines A' and B' are generated in each of planes D and D' by consecutively lighting the luminous units of the planar luminous elements when they are positioned in the detection planes D and D', and by plotting the coordinates of the luminous units of the planar luminous elements when the light-receiving means receives the rays. From this data, the radii of curvature and the axial angle can be obtained by making use of the above equations. In this case, it would be apparent to those skilled in the art that the planar luminous elements may be replaced by straight-line luminous element arrays which are arranged along the X- and Y-axes.

Figure 6A:
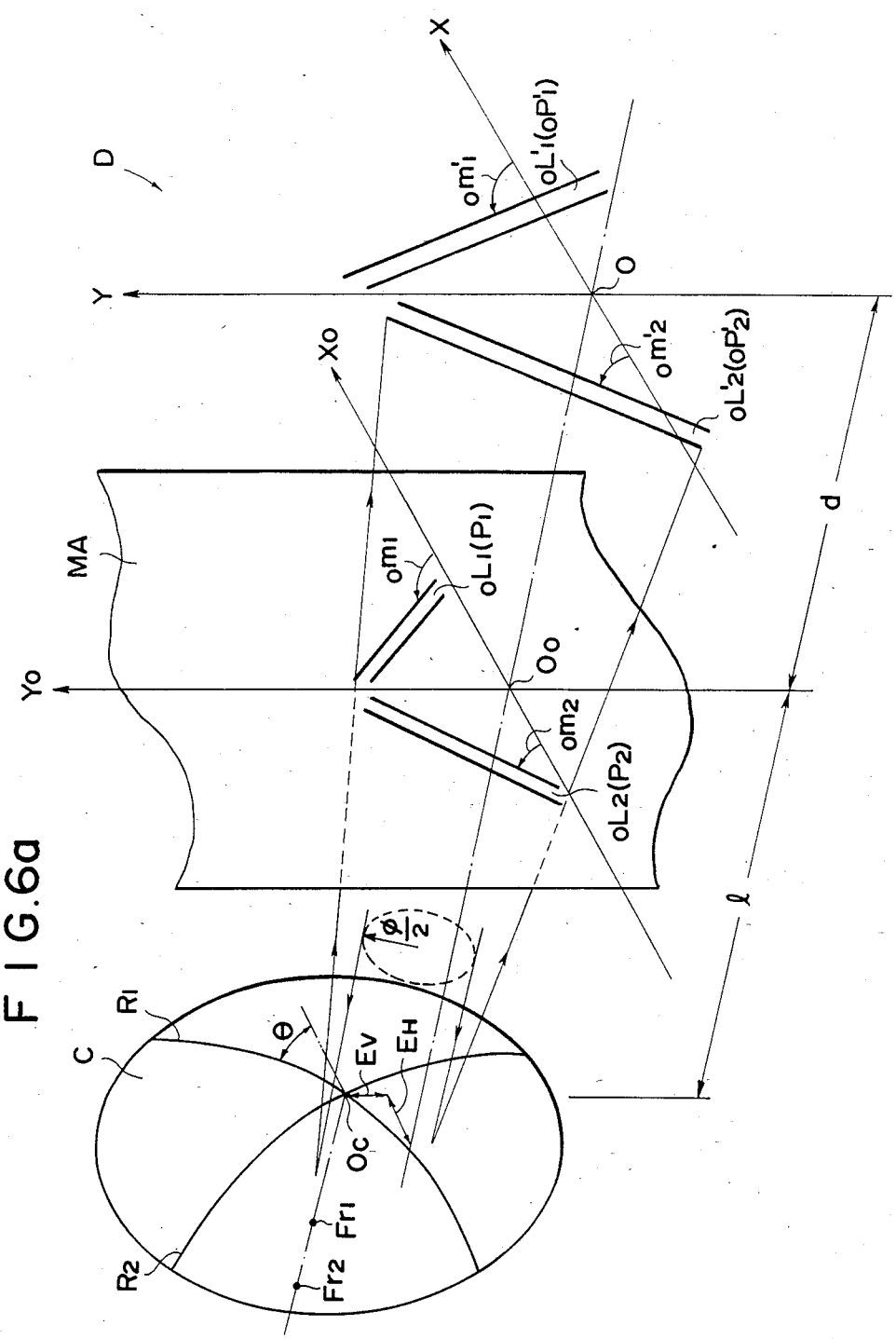
FIG. 6(a) is a perspective view illustrating the second measurement principle of the present invention.

FIG. 6a is a perspective view illustrating the third measurement principle of the present invention, and FIG. 6b is a plan view of the same. In the following description, components identical or equivalent to those of the first measurement principle are indicated with the same reference characters, and their repeated explanations are omitted. The cornea C being measured is illuminated, as shown, by a circular pattern of light having a radius $\phi/2$. The rays of that illuminating light reflected from the cornea C are selectively allowed to pass through straight-line apertures, which are formed in a mask MA at the distance l from the corneal apex $O_C$ and which is defined by the parallel straight line groups $_0L_1$ and $_0L_2$, and are projected upon the detection plane D which is at a distance d from the mask MA. The constructions and arrangements of the straight-line apertures $_0L_1$ and $_0L_2$ are similar to those of the parallel straight-line groups $L_1$ and $L_2$ which are generated by the straight-line light source of the first measurement principle.

The projected parallel straight-line groups $_0L_1'$ and $_0L_2'$ in the detection plane D may be detected, as described in the first measurement principle, either by arranging the plane position sensors in the detection plane or by arranging linear position sensors along the X- and Y-axes. Alternatively, the detections may be conducted by supposing the oblique coordinate system X' - Y' and by arranging linear sensors along the X'- and Y'-axes.

If the projected parallel straight line group $_0L_1'$ has its pitch and inclination changed to $_0P_1'$ and $_0m_1'$, respectively, whereas the projected parallel straight-line group $_0L_2'$ has its pitch and inclination changed to $_0P_2'$ and $_0m_2'$, respectively, and these projected parallel straight-line groups $_0L_1'$ and $_0L_2'$ in the detection plane D are detected, the following equation holds for the inclinations $_0m'$ of each group:

$$_0m' = \frac{_0m[A(l)\sin^2\theta + B(l)\cos^2\theta] + [A(l) - B(l)]\sin\theta \cdot \cos\theta}{_0m[A(l) - B(l)]\sin\theta \cdot \cos\theta + [A(l)\cos^2\theta + B(l)\sin^2\theta]} \quad (16)$$

The change in the pitch P' is expressed by the following equation:

$$\frac{_0P'}{_0P} = A^2(l)\sin^2\theta + B^2(l)\cos^2\theta + \frac{A^2(l) + B^2(l)}{m^2 + 1}[\cos^2\theta + _0m\sin^2\theta] \quad (17)$$

wherein:

$$A(l) = \frac{1 + \frac{2(l+d)}{R_1}}{1 + \frac{2l}{R_1}}$$

$$B(l) = \frac{1 + \frac{2(l+d)}{R_2}}{1 + \frac{2l}{R_2}}$$

On the basis of the present measurement principle, the rays of the parallel luminous flux reflected by the cornea C are selected by the straight-line apertures of the mask MA, and the light thus selected is detected in the detection plane D. It is therefore necessary to set the distance l between the mask MA and the cornea C, i.e., the operating distance, at a constant determined in advance by means of a well-known operating-distance detecting device. It is preferably sufficient to set the distance l at 0.

In the following practical calculations, the curvature characteristics and the alignment of the cornea C may be calculated by applying the above equations (3a) to (16), if necessary, from a virtual parallelogram similarly to the foregoing first measurement principle. Incidentally, since the alignments α and β are dependent upon the distance d between the mask MA and the detection plane D, equation (10) is transformed into the following form for the orthogonal coordinate system X - Y:

$$\alpha = \frac{\sum_{i}^{4} X_i}{4d}$$

$$\beta = \frac{\sum_{i}^{4} Y_i}{4d} \quad \text{and;} \quad (18)$$

equation (15) is transformed into the following form for the oblique coordinate system X' - Y':

$$\alpha = \frac{\sin\alpha \sum_{i}^{4}(X_i' - _0X_i') + \sin\beta \sum_{i}^{4}(Y_i' - _0Y_i')}{4d}$$

$$\beta = \frac{\cos\beta \sum_{i}^{4}(Y_i' - _0Y_i') - \cos\alpha \sum_{i}^{4}(X_i' - _0X_i')}{4d} \quad (19)$$

Figure 7A:
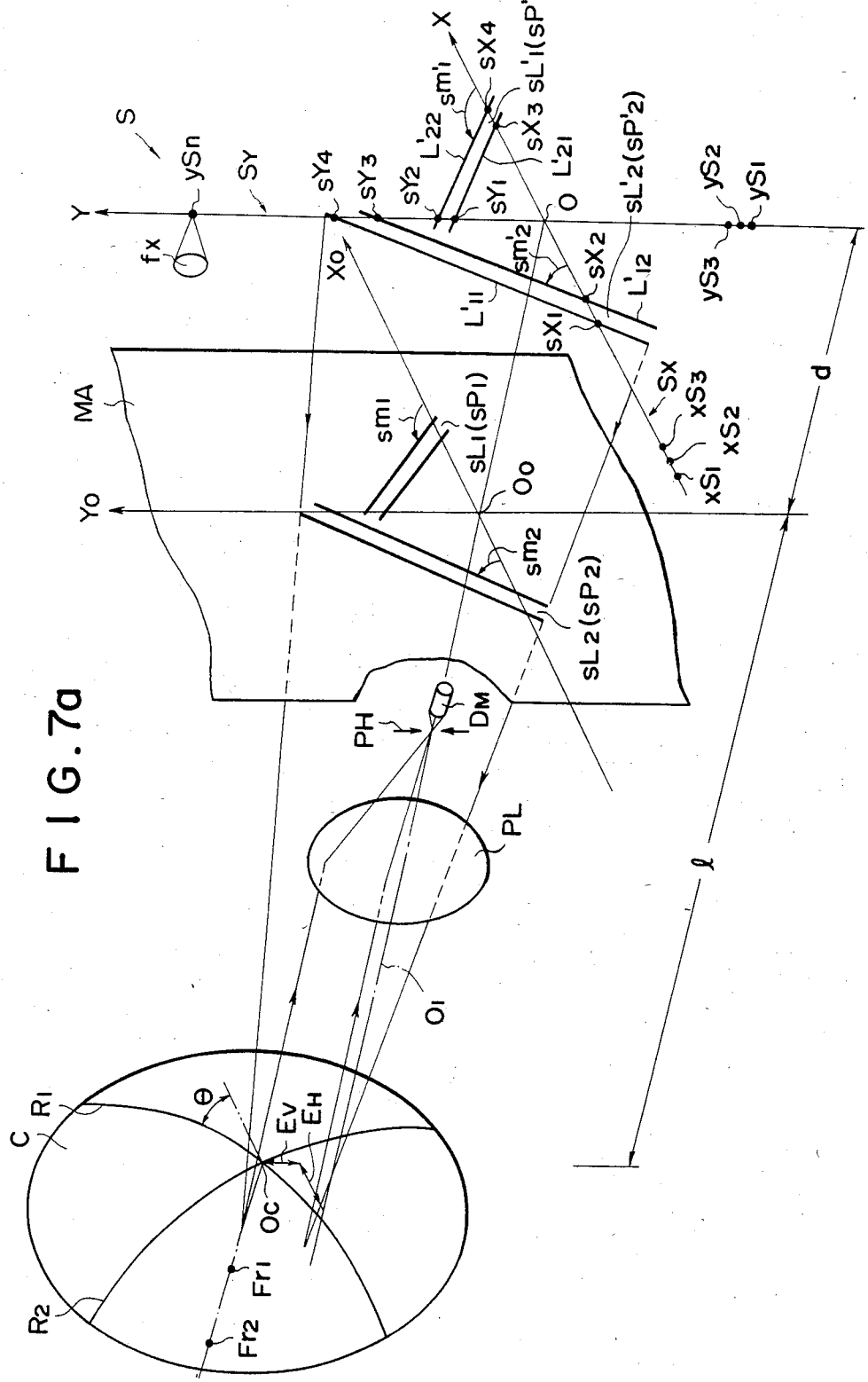
FIG. 7(a) is a perspective view illustrating the third measurement principle of the present invention.

FIG. 7a is a perspective view illustrating a fourth measurement principle of the present invention, and FIG. 7b is a plan view of the same. In the following description, components identical or similar to those of the third measurement principle are designated by the same reference characters, and their explanations are omitted.

This fourth principle is a measurement principle which makes use of the "principle of reciprocity of rays" for the foregoing third principle as is similar to the case in which the "reciprocity principle" is applied to the foregoing first principle thereby to deduce the second measurement principle. More specifically, the illuminating light on the cornea C and the reflected light from the cornea C of the foregoing third principle are assumed to be reversed, and a luminous plane S composed of a plurality of luminuous units is placed in the detection plane D so that the curvature characteristics of the cornea C may be determined from the positions of the luminous units in the luminous plane S which have emitted rays of light from the luminous plane S that have passed through the straight-line apertures of the mask MA and have been reflected by the cornea C so as to be parallel to the optical axis O₁ of the apparatus.

As the luminous element, either a planar luminous element array may be used, in which a plurality of luminous units corresponding to the plane position sensors of the third measurement principle, or a linear luminous element array which corresponds to the linear position sensors and which has its elements intersecting orthogonally or obliquely. FIG. 7a illustrates an example in which a linear luminous element array $S_x$ having light emitting elements $_xS_1$, $_xS_2$, $_xS_3$, - - -, and $_xS_n$, are in a straight-line so as to emit divergent beams of light $f_x$, is arranged along the X axis of the orthogonal coordinate system X - Y whereas a linear luminous element array $X_y$ having luminous elements $_yS_1$, $_yS_2$, $_yS_3$, - - -, and $_yS_n$ is arranged along the Y axis.

A condenser lens PL is arranged on the optical axis O₁ between the mask MA and the cornea C for introducing the rays which have been reflected by the cornea C parallel to the optical axis O₁, into a pin hole PH which is arranged at the focal point. Behind the pin hole PH, a detector $D_M$ is arranged to detect the rays which have passed through the pin hole PH. When the linear luminous arrays $S_x$ and $S_y$ are luminously scanned, the portion of the light coming from certain luminous units $_xS_i$ and $_yS_i$ passes though the apertures of the parallel straight-line groups $_sL_1$ and $_sL_2$ of the mask MA and is reflected by the cornea C. The rays are reflected by the cornea C so as to be parallel to the optical axis O₁, and these parallel rays of light are focused at the pin hole PH by the action of the condensing lens PL and pass through the pin hole PH until they are detected by the detector $D_M$. The luminous units which have emitted the rays when the rays are detected by the detector $D_M$, e.g., the units $_sX_1$, $_sX_2$, $_sX_3$ and $_sX_4$, and $_sY_1$, $_sY_2$, $_sY_3$ and $_sY_4$, are located so that the straight-line loci $L_{11}'$, $L_{12}'$, $L_{21}'$ and $L_{22}'$ can be determined from the luminous points $_sX_1$ and $_sY_4$, $_sX_2$ and $_sY_3$, $_sX_3$ and $_sY_2$, and $_sX_4$ and $_sY_1$, respectively. The parallel straight-line locus groups $_sL_1'$ and $_sL_2'$ are determined from those straight-line loci $L_{11}'$ and $L_{12}'$, and $L_{21}'$ and $L_{22}'$, respectively, and their pitches $_sP_1'$ and $_sP_2'$ and inclinations $_sm_1'$ and $_sM_2'$ are changed from the pitches $_sP_1$ and $_sP_2$ and inclinations $_sm_1$ and $_sm_2$ of the parallel straight-line groups $_sL_1$ and $_sL_2$ of the mask MA in accordance with the curvature characteristics of the cornea C. Between the pitches and inclinations of those parallel straight-line groups $sL_1$ and $sL_2$, and $sL_1'$ and $sL_2'$, moreover, the same relationships as those of equations (16) and (17) of the above third measurement principle hold. Therefore, the curvature characteristics of the cornea C, i.e., the radii of curvature $R_1$ and $R_2$ of the first and second principal meridians, and the axial direction $\theta$ of the same can be determined. Incidentally, in a similar manner as in the third measurement principle, the distance between the mask MA and the cornea C can be predetermined at a constant l, and that the operating distance between the apparatus and the cornea has to be accordingly adjusted.

Upon the practical measurements, incidentally, it is needless to say that a virtual parallelogram may be generated on the basis of the straight-line loci in a similar manner as in the first measurement principle to thereby determine the curvature characteristics of the cornea on the basis of the virtual parallelogram generated. Moreover, it is similar to the thrid measurement principle that the alignments $\alpha$ and $\beta$ follow either equation (16) or (17).

Embodiments based upon the principles of the present invention thus far described will be explained in the following.

FIG. 8 is a view showing the optical arrangement of the ophthalmometer which makes use of the first measurement principle. In the present embodiment, a plane position sensor is used as the detector. It will be apparent from the above explanation of the principle that two parallel of intersecting linear position sensors could be used in place of the plane position sensor.

The ophthalmometer of the present embodiment is constructed mainly of three optical systems, i.e., an illuminating optical system 1, a measuring optical system 2 and a fixed optical system 3.

The straight-line light source of the illuminating optical system 1 may either use a linear luminous element array, in which a plurality of minute luminous elements are arranged in straight lines, or take the following construction. The illuminating optical system 1 has a light source unit 8 which is composed of a light source lamp 4, an infrared filter 5 which allows only the infrared component of the rays coming from the lamp 4 to pass therethrough, a diffusing plate 6 and a condenser lens 7. The rays from the light source unit 8 illuminate an aperture plate 9, as shown in FIG. 9, which is formed with a parallel straight-line group 25 that has at least one thick straight-line aperture 25a and thin straight-line apertures 251, 252, - - -, and 259 arranged in parallel, and a parallel straight-line group 26 that is arranged in a different direction and has a thick straight-line aperture 26a and thin straight-line apertures 261, 262 - - -, and 269 arranged in parallel. The reason why a thick atraight-line aperture 25a or 26a is formed in each of the parallel straight-line groups is to provide references when the equations of the projected straight lines of the other straight-line apertures are to be determined.

The straight-line apertures 25 and 26 of the aperture plate 9 act as the straight-line light sources in the above description of the principles. The rays from the straight-line apertures 25 and 26 pass through the pin hole 10 of a pin-hole plate until they are focused upon a tangential plane H at the apex $O_C$ of the cornea C, by the action of a focusing lens 11. This focusing lens 11 has its focal point positoned at the pin hole 10. As a result, after the illuminating rays of light have passed through the focusing lens 11 and been reflected by a holed half mirror 12 disposed at an angle to the optical axis $O_1$ of the measuring optical system 2, the principal ray illuminates the cornea C parallel to the optical axis $O_1$.

The measuring optical system 2 is arranged with a plane position sensor such as a plane CCD array 13 in a plane which is perpendicular to the optical axis $O_1$. The position sensor 13 has its optically conjugate image focused in the plane D by the action of a holed relay lens 14. This optically conjugate image D is located at such a position that it is not optically conjugate with the aperture plate 9.

An optical-path transforming element 93 is arranged between the relay lens 14 and the position sensor 13 which is made of a glass sheet having parallel faces and which is so arranged that it can be removably inserted into the optical path so as to shift the conjugate image D formed by the relay lens 14 of the position sensor 13 to a positon D'.

The fixed optical system 3 is composed of a light source 80, a condenser lens 81 and a projection lens 83. The visible rays from a fixed index plate 82 pass through the holed relay lens 14 and the holed half mirror 12 as parallel rays, which goes into the eye having the cornea C being measured until it is fixed in that eye. The fixed index plate 82 can be formed, as shown in FIG. 10, of a fixed index 82a of dual concentric type.

In the present embodiment, moreover, in order to generate a reference coordinate system for the measurement instead of the reference coordinate system which has been designwise given in advance for the calculations, a reflecting mirror 90 is arranged in front of the holed half mirror 12 which is formed with a reflecting face normal which is perpendicular to the optical axis $O_1$ of the apparatus and which can be removably inserted into the measuring optical path.

Figure 11:
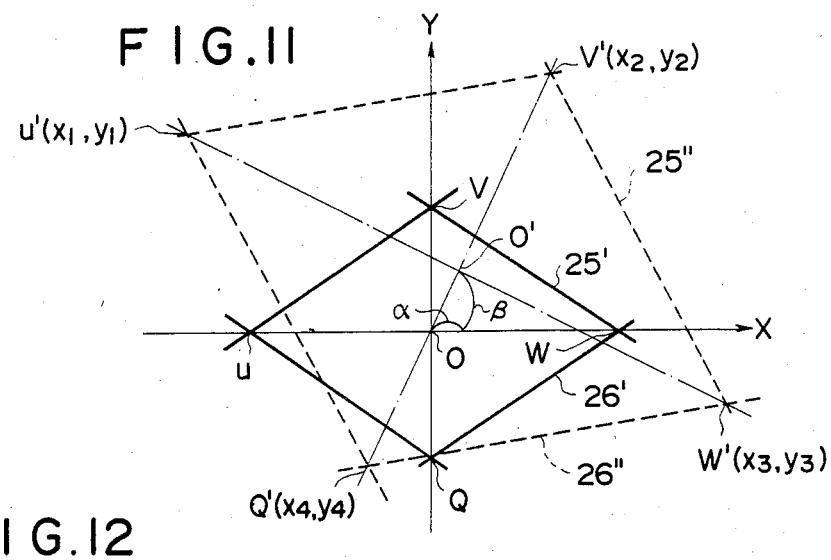
FIG. 11 is a schematic view illustrating the detection of the alignments.
Figure 12:
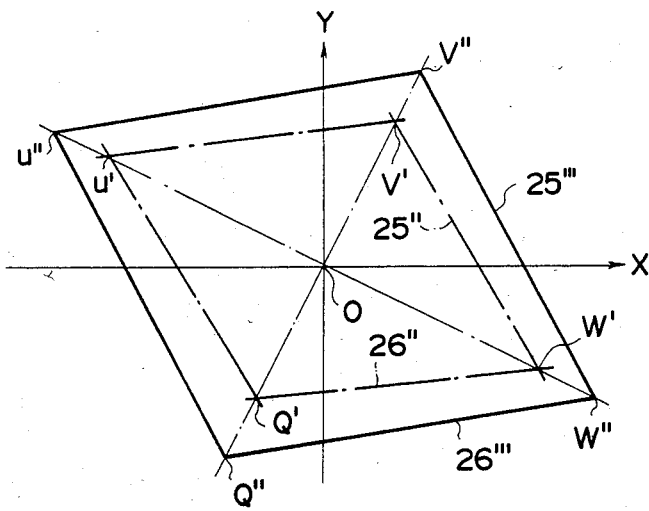
FIG. 12 is a schematic view illustrating the relationship of the virtual parallelograms of the first embodiment.

During the measurements, a reflecting mirror 90 is first inserted while the optical-path transforming element 93 is inserted into the measuring optical path, by the action of a actuator (not shown), and the light source 4 is then lit. The parallel straight-line groups 25 and 26 of the aperture plate 9 are made to act as straight-line light sources using the light from the light source 4 so that the rays of light emanating therefrom irradiate the reflecting mirror 90. The rays reflected from the reflecting mirror 90 are reflected parallel to the optical axis $O_1$ and shine on the position sensor 13 through the relay lens 14 so that the projected straight-line groups are detected. This is schematically illustrated in FIG. 11. A virtual parallelogram UVWQ is generated on the basis of the above measurement principle from the projected straight lines 25' and 26' of the projected straight-line groups, which correspond to the parallel straight-line groups 25 and 26, thereby defining an X - Y coordinate system which has as its X-axis the line joining the apexes U and W of the parallelogram, and as its Y-axis the line joining apexes V and Q. From now on, the X - Y coordinate system thus defined will be used as the reference coordinate system for the measurements and calculations. Next the reflecting mirror 90 is removed from the measuring optical path, and the cornea C being measured is irradiated with the rays coming from the straight-line light sources 25 and 26. The rays reflected from the cornea C pass through the relay lens 14 and are detected by the position sensor 13 defining a virtual parallelogram U'V'W'Q' from the projected straight lines 25" and 26". The four apexes of that virtual parallelogram have their coordinates located at U'($x_1$, $y_1$), V'($x_2$, $y_2$), W'($x_3$, $y_3$) and Q'($x_4$, $y_4$), and the alignment differences α and β are calculated from equation (10). The apparatus is traversed horizontally and vertically in accordance with these alignment differences by the action of a traversing mechanism (not shown) until alignment is reached. When the alignment is completed, as shown in FIG. 12, the optical-path transforming element 93 is removed from the measuring optical path, and the position of the conjugate detection plane used for the detection until that time is shifted from D' to D. The position sensor 13 is again scanned to detect the projected straight lines so that a virtual parallelogram U″V″W″Q″ is defined from the projected straight lines 25‴ and 26‴ detected. The coordinates of the four apexes of that virtual parallelogram are located at U″($x_1 t'$, $y_1'$), V″($x_2'$, $y_2'$), W″($x_3'$, $y_3'$) and Q″($x_4'$, $y_4'$), and equations (3) to (5) are applied to the coordinates of the four apexes of the previous virtual parallelogram U'V'W'Q' so that the curvature characteristics of the cornea C being measured, i.e., the radii of curvature of the first and second principal meridians and the axial angle θ of the same, may be calculated.

Figure 13:
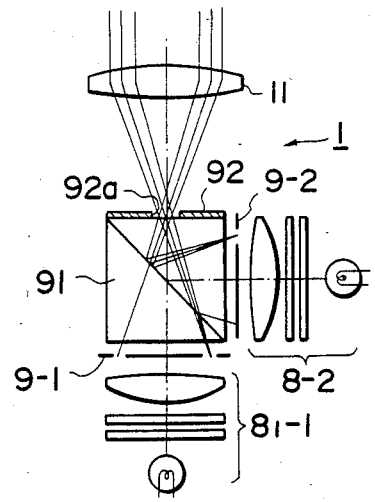
FIG. 13 is a view illustrating the optical arrangement of just the illuminating optical system of a second embodiment of the present invention.

FIG. 13 is a second embodiment of the present invention, showing the way in which the straight-line light sources 25 and 26 of the illuminating light source 1 of the above first embodiment are made, and is a view showing the optical arrangement of part of the illuminating optical system 1.

In the first embodiment, the parallel straight-line groups 25 and 26 acting as the straight-line light sources are formed on the single aperture plate 9. In the present embodiment shown in FIG. 13, separate aperture plates are formed, each with a parallel straight-line group so that the two parallel straight-line groups are formed when they are focused on the tangential plane H by the action of the focusing lens 11.

The illuminating optical system 1 of the present embodiment is equipped with two light source units 8-1 and 8-2 each of which has a construction similar to that of the light source unit of the first embodiment and which are arranged with respective aperture plates 9-1 and 9-2. The aperture plate 9-1 is formed with a parallel straight-line group which corresponds to the parallel straight-line group 25 of FIG. 9, and the aperture plate 9-2 is formed with a parallel straight-line group which corresponds to the parallel straight-line group 26. The rays of light emitted from the aperture plates 9-1 and 9-2 are combined by means of a half mirror 91, and the combined rays pass through the pin hole 92a of a shielding film 92, which is formed on the upper face of the half mirror 91, into the focusing lens 11. The subsequent operations are similar to those of the first embodiment.

In order to modify the embodiment thus far described to the second measurement principle by applying the "principle of reciprocity of rays", a luminous element array, which has multiple infrared-luminous elements arranged in a plane, is arranged at the position of the position sensor 13, and a planar light-receiving element having its light-receiving units only at the same places as the aperture pattern of the aperture plate 9 is arranged at the position of the aperture plate 9. As an alternative, the light-receiving element can be placed at the position of the light source lamp 4 so that, when the light-receiving element receives light, the luminous element that emitted that light may be located to determine the radii of curvature and the axial angle. In this case, too, various modification can be made in a similar manner as in the previous embodiments.

FIG. 14 is an optical arrangement view showing a third embodiment of the present invention. This embodiment relates to an ophthalmometer which makes use of the above third measurement principle. Components identical or equivalent to those of the first embodiment are indicated with the same reference characters, and their explanations are omitted.

In the present embodiment, two linear position sensors are used as the detector in combination with a half mirror in a manner in which images obliquely intersect in the conjugate detection plane. However, the present invention should not be limited thereto but can be modified, as is apparent from the description of the principle, in such a way that the detection can be made by the use of a plane position sensor, two intersecting linear position sensors or two parallel position sensors.

Two infrared light-emitting diodes 70 and 71 which are different in the wavelength of their emitted rays are used as the light source of the illuminating optical system 1. The rays from the light-emitting diode 70 pass through the dichroic face 72a of a dichroic prism 72 and enter the condenser lens 7. Similarily, the rays from the light-emitting diode 71 are reflected by the dichroic face 72a and likewise enters the condenser lens 7.

The rays emitting from the condenser lens 7 pass through the pin hole of the pin-hole plate 10 and are collimated into a parallel beam of light by the action of a collimator lens 73 having its focal point located at the pin hole. After that, the parallel beam of light is reflected by a small mirror 85, which is disposed at an angle to the optical axis $O_1$ of the apparatus, so that if shines on the cornea C parallel to the optical axis $O_1$. The fixed index image of the fixed optical system 3 illuminates the eye by the action of a half mirror 84 which is disposed at an angle in the illuminating optical system 1.

A dichroic mirror 86, the rear optical path of which is divided into two, i.e., a first optical path 120 and a second optical path 121, is arranged behind the relay lens 14.

A mask 13a is arranged in the first optical path, and a mask 13b is arranged in the second optical path 121. The rays of light passed through the mask 13a are further divided into two by the action of a half mirror 303 so that the reflected rays of light enter the linear position sensor 15 whereas the other rays of light enter the linear position sensor 16. Similarily, the rays of light passed through the mask 13b are also reflected by and allowed to pass through the half mirror 303 so that the two rays respectively enter the linear sensors 16 and 15. The linear sensors 15 and 16 are so arranged by the relay lens 14 that their conjugate detection planes D intersect.

The conjugate images of the masks 13a and 13b are formed at a position MA by the action of the relay lens 14. These conjugate planes MA and D have an optically non-conjugate relationship with the pin hole 10.

FIGS. 15a and 15b illustrate the mask patterns of the above light-restricting masks 13a and 13b, respectively.

The mask 13a has a parallel straight-line group 20 which is formed of a plurality of straight lines having an inclination $m_2$ and pitch p. At least one of the straight lines of the parallel straight-line group 20 is further formed as a reference straight line 22 having a different thickness so that it can be discriminated from the remaining straight lines. Likewise, the mask 13b has a parallel straight-line group 21 which is formed of a plurality of straight lines having an inclination $m_1$ and pitch p, and a reference straight line 23.

In the present embodiment, the reference straight lines 22 and 23 are discriminated from the other straight lines by having different thicknesses. However, the present invention should not be limited thereto, the reference straight lines may be discriminated by making the optical transmissivities or the transmission wavelength characteristics different, or straight-line groups of identical width but with a pitch that changes at specific places may be used in place of the reference straight lines.

The images of respective parallel straight-line groups 20 and 21 of the masks 13a and 13b are so constructed on the common conjugate plane MA of the masks 13a and 13b by the relay lens 14 of FIG. 14 that they intersect at an angle $\theta$ and that the bisector 24 of that angle intersects a certain reference axis 25 at an angle $\epsilon$. In the present embodiment, $\theta = 90$ degrees, and $\epsilon = 90$ degrees.

Incidentally, the pitches of the parallel straight-line groups 20 and 21 selected have an identical value P. However, this is intended only to facilitate the fabrication of the masks 13a and 13b. Therefore, it is sufficient to use parallel straight-line groups having different pitches, and it is unnecessary to make the pitches of the straight lines of a parallel straight-line group identical.

Moreover, the angles $\theta$ and $\epsilon$ may also be selected arbitrarily. FIG. 16 is a view illustrating the projected relationship of the mask pattern images upon the linear sensors when the mask pattern images are detected by the linear sensors. As illustrated in FIG. 16, the linear sensors 15 and 16 of FIG. 14 are arranged in such a relationship that they intersect at an angle $\gamma$ in the common conjugate plane, i.e., the detection plane D, formed by the action of the relay lens 14. The rays of light bearing the information on the curvature characteristics of the cornea C passes through the masks 13a and 13b so that the parallel straight-line group 20 of the mask 13a is projected as straight lines 20'a, 20'b, 22, - - -, and 20'h on the linear sensors 15 and 16. Similarily, the parallel straight-line group 21 of the mask 13b is projected as straight lines 21'a, 21'b, - - -, 23, - - - and 21'i. These projected straight lines have their pitches changed to p' and p'', respectrively, their mutual intersection angle changed to $\theta'$, and the intersection angle, at which the bisector 24' intersects a reference axis 25', is changed to $\epsilon'$ by the curvature characteristics of the cornea C.

During the measurements, the first measuring optical path is formed by the illumination of the light source 70 so that the straight lines 20'a, 20'b, - - -, 22', - - -, and 20'h projected by the mask 13a are projected on the linear sensors 15 and 16. The projected straight lines 20'a, 20'b, - - -, and 20'h are detected at detection points $e_{11}$, $e_{12}$, - - -, and $e_{17}$, by the linear sensor 15. At the same time, the projected straight lines are detected at detection points $f_{11}$, $f_{12}$, - - -, $f_{19}$ by the linear sensor 16.

When the light source 71 is lit, the second measuring optical path is formed so that straight lines 21'a, 21'b, - - -, 23', - - - and 21'i projected by the mask 13b are projected on the linear sensors 5 and 16. The projected straight lines 21'a, 21'b, - - -, 23', - - -, and 21'i are detected at detection points $e_{21}$, $e_{22}$, - - -, $e_{29}$, and $e_{20}$, by the linear sensor 15, and the projected straight lines are similarly detected at detection points $f_{21}$, $f_{22}$, - - -, and $f_{26}$ by the linear sensor 16.

FIGS. 17(A) to (M) are timing charts illustrating the linear sensor outputs when the projected straight-line patterns are detected by the linear sensors, and the subsequent calculations. Figure 17(A) is a pulse train for reading and driving the detected outputs of the linear sensors so that the detected outputs are consecutively fed out of the linear sensors when the pulses are received by the linear sensors. FIG. 17(B) illustrates the waveform (i.e., the envelope) of the detected output of the linear sensor 15 when the projected straight lines 20'a, 20'b, - - -, 22', - - -, and 20'h are projected on the linear sensor 15. The level of the output waveform of FIG. 17(B) rises at points corresponding to the detection points $e_{11}$, $e_{12}$, - - -, $e_{17}$. Likewise, FIG. 17(C) illustrates the output waveform for the straight lines 20'a, 20'b, - - -, and 20'h detected by the linear sensor 16. FIG. 17(D) illustrates the output waveform of the straight lines 21'a, 21'b, - - -, 23, - - -, and 21'i detected by the linear sensor 15, and FIG. 17(E) illustrates the output waveform of the projected straight lines 21'a, 21'b, - - -, 23', - - -, and 21'i detected by the linear sensor 16. FIGS. 17(F) to (I) illustrate square output waveforms which are shaped by a Schmidt trigger circuit from the above detected output waveforms (B) to (E) and which correspond to the output waveforms (B) to (E), respectively. The centers of each of the pulses of the square output waveforms (F) to (I) thus generated are them identified by making use of the numbers of the sensor elements of the linear sensor as a scale.

As illustrated in FIG. 18, more specifically, when the $E_p$th to $E_{p+n}$th sensor elements of a linear sensor LNS composed of a number N of sensor elements $E_1$, $E_2$, - - -, $E_{N-1}$ and $E_N$ generates a square-wave output $e_A$, whereas the $E_l$th to $E_{l+m}$th sensor elements generates a square-wave output $e_B$, the width $\Delta_A$ of the square-wave output $e_A$ corresponds to a number n of sensor elements, and the width $\Delta_B$ of the square-wave output $e_B$ corresponds to a number m of sensor elements. It is, therefore, understood that the center $O_1$ of the output pulse $e_A$ corresponds to the $E_{c1}$th ($= E_{p+n/2}$) element which is shifted from the $E_p$th element by n/2. Likewise, the center $O_2$ of the output pulse $e_B$ corresponds to the $E_{c2}$th ($= E_{1+m/2}$) element. In order to enhance the detection presision, moreover, it is necessary to interpolate the space between the pitches of the sensor elements. This is achieved by shaping the waveforms at a suitable slice level after the rise and fall protions of the output signal have been precisely detected by the envelopes, and by locating the centers by the use of clock pulses which have a sufficiently higher frequency than the pulse train driving the linear sensor.

Thus the positions of the projected straight-line patterns are obtained as coordinate values, which are located by the element numbers of the linear sensors, i.e., which use the linear sensors as coordinate axes, by locating the centers of the square output pulses of the linear sensors, which are extracted from the detection points.

FIGS. 17(J) to (M) are charts illustrating each set of detection points obtained by the above method as coordinate values along the linear sensors.

The coordinate values $e'_{11}$, $e_{12}'$, - - -, and $e'_{17}$ correspond to the detection points $e_{11}$, $e_{12}$, - - -, and $e_{17}$, respectively. Similarily, the coordinate values $f'_{11}$ to $f'_{19}$ correspond to the detection points $f_{11}$ to $f_{19}$, the coordinate values $e'_{21}$ to $e'_{20}$ correspond to the detection points $e_{21}$ to $e_{20}$, and the coordinate values $f'_{21}$ to $f'_{26}$ correspond to the detection points $f_{21}$ to $f_{26}$.

Figure 17:
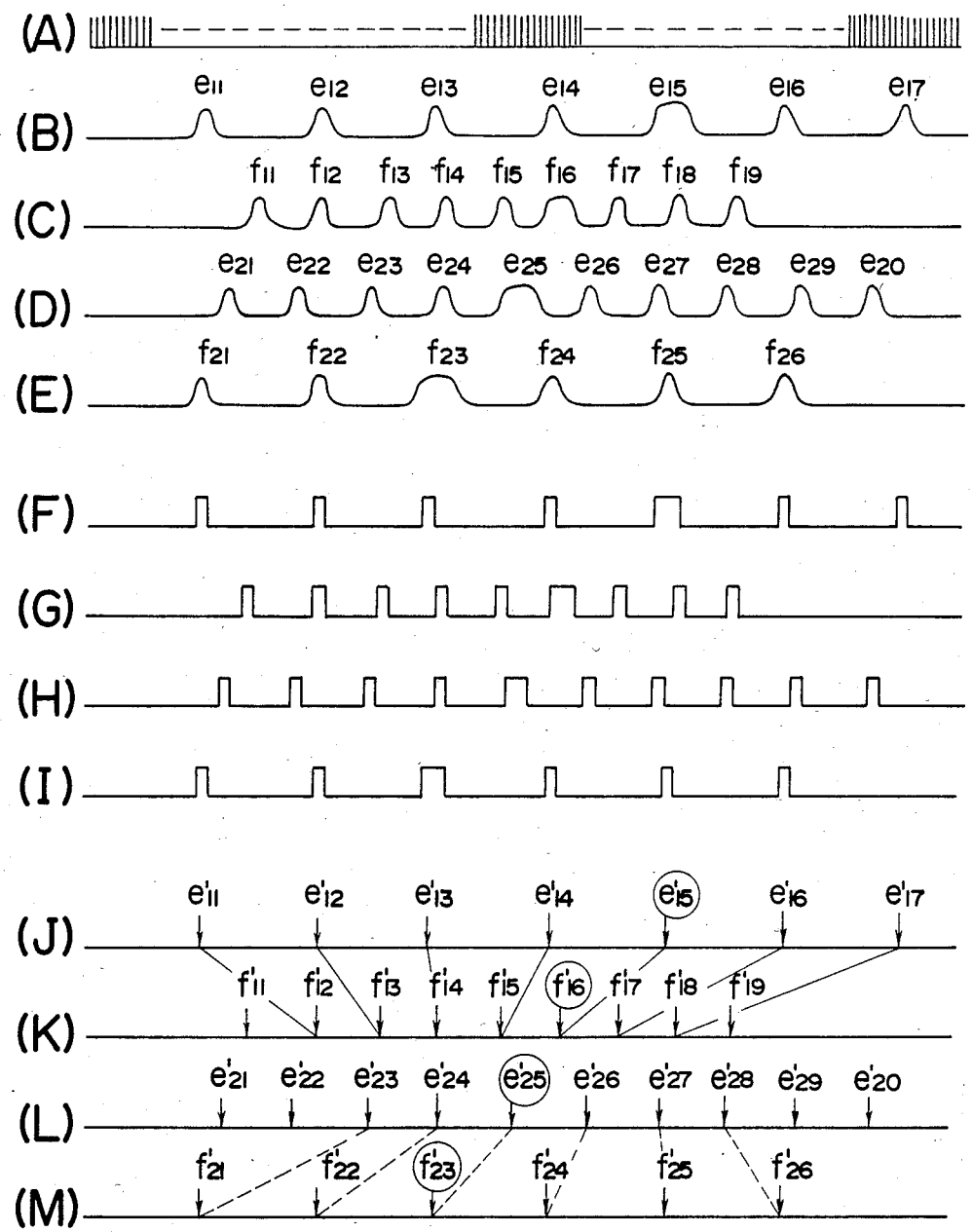

As illustrated in FIG. 18, the number m of sensor elements generating the square-wave output pulse $e_B$ is different from the number n of sensor elements generating the square-wave output pulse $e_A$, and the inequality m > n holds. It is, therefore, found that the output pulse $e_B$ is the detected output of a projected straight-line pattern generated by such reference straight lines as are illustrated in FIGS. 15a and 15b. It is also found in the present embodiment that the detection points $e_{15}$, $f_{16}$, $e_{25}$ and $f_{23}$ of FIGS. 16 and 17 are the detection points at which the reference projected straight lines 22' and 23' are detected, and the detection points $e'_{15}$, $f'_{16}$, $e'_{25}$ and $f'_{23}$ are the respective reference coordinate values.

The equation of the reference projected straight line 22' can be determined from the reference coordinate values $e'_{15}$ and $f'_{16}$, and the equation of the reference projected straight line 23' can be determined from the reference coordinate values $e'_{25}$ and $f'_{23}$. Similarily, the equations of the other projected straight lines can be determined from the respective coordinate values which are identified with reference to the reference coordinate values $e'_{15}$, $f'_{16}$, $e'_{25}$ and $f'_{23}$. For example, the equation of the projected straight line 20'$f$ can be determined from the coordinate value $e'_{16}$ next to the reference coordinate value $e'_{15}$ and from the coordinate value $f'_{17}$ next to the reference coordinate value $f'_{16}$. Thus, the equations of the plurality of projected straight lines can be determined from the respective coordinate values, and because the projected straight lines belonging to the same parallel straight-line group remain parallel, more precise and fine detection results can be obtained by averaging those numerous linear equations. It is also possible to determine the values of the pitches P' of the numerous equations extracted and to determine the precise and fine pitches P' by averaging these numerous values. This possibility is a major feature of the present invention.

Next, with reference to FIGS. 19 to 21, a method will be described by which virtual straight lines are generated from the equations of the projected straight-line patterns detected by the linear sensors and by which four arbitrary points are determined in the same plane as the plane of the projected straight-line patterns so that the curvature characteristics of the cornea being measured may be measured from the changes in those four points. FIG. 19 illustrates the case in which the straight-line patterns 20 and 21 are projected on the linear sensors 15 and 16 when the cornea C is not in the measuring optical path but the reflecting mirror 90 is inserted thereinto. The projected straight-line patterns 20'' and 21'' (note that only the projected reference straight lines 22'' and 23'' and the straight lines 20''$e$, 20''$f$, 21''$d$ and 21''$e$ are illustrated in FIG. 19) have their straight-line equations and their pitches determined by the above method. It is possible to generate a virtual straight line 30 having an inclination of $f \times m_2$ at a position at a distance of $e \times P$ from the projected straight line 20''$e$, and to generate a virtual straight line 31 having an inclination of $f \times m_2$ at a distance of $g \times P$ on the opposite side. By a similar method, a straight line 32 having an inclination of $f \times m_1$ is generated at a distance of $h \times P$ from the straight line image 21''$d$, and a straight line 33 having an inclination of $f \times m_1$ at a distance of $i \times P$. Here the coefficients e, f, g, h and i are selected arbitrarily so that virtual straight lines having the same inclinations as those $m_1$ and $m_2$ of the equations of the straight line images are usually generated with $f=1$. Moreover, the coefficients e, g, h and i are so selected that the intersection points 36, 37, 38 and 39 of the virtual straight lines generated are symmetrical with respect to the center 34 of the mask. FIG. 19 illustrates the state in which the virtual straight lines are generated in this way. If the virtual straight lines are generated in this way, it is easy to calculate the alignments with the cornea, as has already been described in the explanation of the principles.

FIG. 20 illustrates a method in which the apparatus is shifted to retract the reflecting mirror 90, so that the cornea to be measured is in the measuring optical path, and in which the projected straight-line patterns generated by the rays of light changed by the curvature characteristics of that cornea are detected by means of line sensors so that virtual straight lines may be determined from those straight-line patterns. In the following description, incidentally, it is assumed that the adjustment of the alignment between the cornea and the measuring optical axis has already been completed by a method similar to that of the first embodiment.

First of all, the projected straight-line patterns 20' and 21', with their pitches and inclinations changed to P' and P'' and to $m_1$, and $m_2'$, respectively, by the curvature characteristics of the cornea, are detected to determine their equations, as has been described before. Next, the virtual straight line 30' is generated at a distance of $e \times P''$ by using the same coefficient e as that used for generating the virtual straight line 30 in FIG. 17 with reference to the projected straight line 20'$e$ 0 corresponding to the projected straight line 20''$e$ which was used as a reference in FIG. 19. Incidentally, since the coefficient f of the inclination of $f \times m_2$ of the virtual straight line 30' of FIG. 19 is set at 1, the coefficient f of the inclination of $f \times m_2'$ of the virtual straight line 30 is similarly set at 1. By a similar method a virtual straight line 31' is generated at a distance of $g \times P''$ from the projected straight line 20'$e$, a virtual straight line 32' is generated at a distance of $h \times P'$ from the projected straight line 21'$d$, and a virtual straight line 33' is generated at a distance of $i \times P'$. Four intersection points 36', 37', 38' and 39' are generated from these virtual straight lines 30', 31', 32' and 33', and their center obtained.

The four points 36 to 39 thus determined are shifted in the detection plane D to the four points 36' to 39' respectively by the curvature characteristics of the cornea being measured. This is illustrated in FIG. 21. The curvature characteristics of the lens being measured can be calculated on the basis of those shifts by equations (3) to (5). If the method is used in which the four intersection points of the virtual straight lines generated when the cornea being measured is not in the measuring optical path, but the plane reflecting mirror is inserted into the measuring optical path, are used as reference points to determine the shifts of those four points when the cornea is in the measuring optical path, the above three equations become absolutely invariant for the coordinate system generated by the two linear sensors. This results in the remarkable advantage that it is unnecessary to control the intersection angle and the intersection position of the linear sensors during assembly.

FIG. 22 is a block diagram showing a simplified form of one example of the processing circuit for executing the calculations thus far described. The linear sensors 15 and 16 driven by linear sensor drivers 100 and 101, respectively, ｒｅａｄ, as illustrated in FIGS. 15(B) to (C), the detected output signal of the straight-line patterns projected by the light-restricting mask 13a to signal lines 102 and 103 respectively in response to the illumination of the light source 70 driven by a drive circuit 60. Reference numeral 104 indicates an analog switch which is controlled by a micro processor 105. This micro processor 105 controls the analog switch when it is interrupted in response to the scanning starting pulses 106 of the linear sensor by the action of the driver 100 driving the linear sensor 15 so that the output of the linear sensor 15 may be fed to and A/D converter 107. This A/D converter 107 converts the output of each element of the linear sensors to digital signals, which are read out in response to linear sensor reading pulses 108 output from the driver circuit 100 (as illustrated in FIG. 17(A)) to feed the converted digital values to the micro processor. The A/D converter 107 is selected to have a resolution of about 8 bits (1/256) and a faster conversion speed than the scanning frequency of the linear sensors. The micro processor 105 reads the output of the linear sensor 15, which has been converted for each element into a digital value, and stores them sequentially in a data memory 109 which is a RAM (Ramdom Access Memory) or the like. As a result, the data memory 109 is consecutively stored with the output of the first element of the linear sensor in the form of a digital value in accordance with a predetermined position (or address). If the linear sensor has 1728 elements, for example, the micro processor 105 stops interrupting its data reading operations when the reading operations of the 1728 items of data ends, and waits for a interruption by scanning the starting pulses 110 driving the linear sensor 16. When interrupted, the micro processor 105 controls the analog switch 104 to thereby subsequently store the output of the linear sensor 16, which is read out by linear sensor reading pulses 111, in the form of digital values, in the data memory 109. Next, the micro processor 105 controls the drive circuit 60 to extinguish the light source 70, which has been emitting its light until that time, and light the light source 71. By a process similar to the above one, the detected outputs of FIGS. 17(D) and (E) are stored as digital values in the data memory 109. At this stage, all the measured data is stored in the data memory 109. After that, an arithmetic circuit 112 in the micro processor 105 executes the following calculations on the basis of the data written in the data memory 109:

(1) The arithmetic circuit 112 detects at what element number of the linear sensor the centers of each of the output pulses generated by the projected images of the straight-line patterns of the luminous flux restricting mask are located.

(2) The arithmetic circuit 112 determines the equations of the straight-line pattern images in the coordinate system defined by the two linear sensors.

(3) The arithmetic circuit 112 uses the above method to determine the equations of virtual straight lines such as 30' to 33' of FIG. 20 and to locate the coordinate positions of the four points 36' to 39' of FIG. 27 as the intersection points of those straight lines thereby determing the center position 34'.

(4) The arithmetic circuit 112 executes its operations in accordance with equations (3) to (5) from the reference positions 36 to 39 of the four points and the coordinate position of their center 34, when the reflecting mirror 21 is inserted in the measuring optical path, and from the reference positions 36' to 39' and the coordinate position of the center 34', determined in (3) above, thereby determing the radius of curvature $R_1$ of the first principal meridian, the radius of curvature $R_2$ of the second principal meridian, the axial direction $\theta$ and the alignments $\alpha$ and $\beta$ of the cornea being measured.

The values thus obtained by the calculations thus far described are fed to an indicator 113 and a printer device 114, both of which are shown in FIG. 22.

Incidentally, it is convenient for measurements that a well-known CRT display device is used as the indicator and that the alignments $\alpha$ and $\beta$ are displayed. Moreover, if these alignments $\alpha$ and $\beta$ are fed as electric signals to a driven section 117 of the apparatus casing so that the section 117 is electrically driven in accordance with the electric signals, autoalignment can be achieved.

The processings thus far described are all conducted in accordance with a program which is recorded in a program memory 115. It is not special but can be easily achieved by those skilled in the art that these processings are executed by a microprocessor.

The present invention should not be limited to the embodiments thus far described but can enjoy a variety of modifications. Two or three examples will now be disclosed in the following.

FIG. 23 is a view showing the optical arrangement of part of a fourth embodiment of the present invention. The illuminating optical system and the fixed optical system are similar to those of the third embodiment, and their illustrations and explanations are omitted. Similar constructional components are indicated with identical reference characters, and their explanations are omitted.

A second relay lens group 87 is arranged behind the relay lens 14 in the measuring optical system 2, and a mask plate 9 similar to that shown in FIG. 9 is interposed between the relay lens group 87 and the relay lens 14. The mask plate 9 forms a conjugate image at position MA in the figure by the action of the relay lens 14. Behind the second relay lens 87, the dichroic mirror 86 is disposed whose reflecting and transmitting optical paths form the first and second optical paths, respectively. The second optical path 121 is provided with an image rotator 125 for rotating the image through a predetermined angle on the optical axis. The first and second optical paths 120 and 121 are combined by a dichroic mirror 123. Behind this mirror 123, a third relay lens 124 is provided, behind which is the linear position sensor 15. This linear sensor 15 forms a conjugate image at position D in the figure by the actions of the relay lens 14, the second relay lens group 87 and the third relay lens 124. Moreover, since the image rotator 125 is provided in the second optical path 121, as described above, the linear sensor 15 is equivalent to two intersecting linear sensors in the conjugate detection plane D.

During the measurements, the rays reflected from the cornea C are selectively allowed, when emitted from the illuminating light source 70, to be transmitted through the parallel straight-line groups 25 and 26 of the light-restricting mask 9 so that they passes along the first optical path 120 until they are projected as the projected parallel straight-line groups 25' and 26' on the linear sensor 15. The resultant projected patterns are detected at the detection points $e_1$, $e_2$, - - - , and $e_6$ by the linear sensor 15, as illustrated in FIG. 24. Next, if the illuminating light source is switched to 71, the rays reflected from the cornea are similarily selected by the parallel straight-line groups 25 and 26 of the mask 9 so that the selected light passes along the second optical path 121 until it is rotated by the image rotator. This rotation is equivalent to the arrangement in which the linear sensor 15 is positioned at 15', as illustrated in FIG. 24. Thus, the projected parallel straight-line groups 25' and 26' of the parallel straight-line groups 25 and 26 are detected at the detection points $f_1$, $f_2$, - - - , and $f_6$.

In the following, the method for determining the virtual parallelogram on the basis of those detection points to calculate the curvature characteristics of the cornea being measured is similar to that of the foregoing second embodiment.

The measurements can be conducted even if the linear sensors 15 and 16 of the third embodiment (shown in FIG. 14) are so arranged by the relay lens 14 that they are parallel to each other in the conjugate plane D. As illustrated in FIG. 25, moreover, if light-shifting means 301 made of a glass plate having parallel faces is arranged behind the relay lens group 87 and is rotated to the four positions (A), (B), (C) and (D) about an axis which is perpendicular to the optical axis $O_1$, the rays of light reflected from the cornea C selected by the flux restricting mask 9 are shifted in a manner equivalent to the construction in which four parallel linear sensors 15 are arranged in the conjugate plane D, as illustrated in FIG. 26. As a result, two points of each of the projected straight lines of the projected parallel straight-line groups 25' and 26' are detected so that their equations can be determined. Thus a virtual parallelogram is generated so that the curvature characteristics of the cornea C can be measured in a similar manner as that of the previous embodiments.

It will be easily understood from the fourth embodiment that, if the image rotator is rotated about the optical axis $O_1$ instead of the flux shifting means 301 of FIG. 25, each of the projected parallel straight-line groups can be detected, as illustrated in FIG. 22.

Moreover, it is sufficient to detect the projected patterns by rotating the linear sensor 15 about the optical axis $O_1$ by means of a pulse motor 302, which is rotationally controlled by a pulse motor drive circuit 303, as shown in FIG. 27, instead of an image rotator.

FIG. 28 is a view showing the optical arrangement of a seventh embodiment of the present invention. The present embodiment relates to an ophthalmometer to which the above measurement principle is applied. Incidentally, although the present embodiment makes use of a plane luminous element array, it will be apparent to those skilled in the art that a linear luminous element array can take the place of the plane luminous element array even in an ophthalmometer making use of the fourth measurement principle, as in the previous various embodiments in which the linear position sensors can be replaced by linear light-receiving element arrays. A plane luminous element array 320 is arranged in a plane which is normal to the optical axis of the relay lens 14. The plane luminous element array 320 is constructed so as to have tiny light-emitting diodes densely arranged on a plane substrate. The light-restricting mask 9, which is similar to that of the foregoing third embodiment, is interposed between the relay lens 14 and the luminous element array 320 so that the mask 9 has its conjugate image formed at position MA whereas the luminous element array has its conjugate image formed at position S by the action of the relay lens 14. This relay lens 14 also acts as the condenser lens L, which has already been described in the above description of the principles, thereby condensing the rays of the light reflected by the cornea C into a pin hole 322 through a reflecting mirror 321 that is parallel to the optical axis O of the relay lens 14 so that the rays passing through the pin hole 322 are introduced into a detector 324 by the action of a relay lens 323. A avalanche photodiode having a high sensitivity is used as the detector 324. In order to enhance the sensitivity, moreover, it is sufficient to use either an electrically cooling means making use of the Peltier effect or a well-known photo multiplier.

In the measuring method, the diodes of the plane luminous element array 320 are consecutively scanned so that the rays from some of the scanned light-emitting diodes pass through the parallel straight-line groups 25 and 26 of the mask 9 so that they shine on the cornea C. The rays are then reflected by the cornea C so that they are partially condensed into the pin hole 322 by the action of the relay lens 14 and they are detected by the detector 324. From the positions of the light-emitting diodes when the detection is made by that detector 324, e.g., the luminous points $e_1$, $e_2$, - - -, and $e_6$, and $f_1$, $f_2$, - - -, and $f_6$ of FIG. 24, the straight-line loci 25' and 26' are calculated, upon which a virtual parallelogram is generated so that the radii of curvature $R_1$ and $R_2$ and the axial angle $\theta$ of the cornea are calculated by using equations (3) to (5).

The driven arithmetic circuit of the present embodiment can be achieved by a construction that is substantially similar to that of the circuit of FIG. 22. One example is shown in FIG. 32. The constructional components identical or equivalent to those shown in FIG. 22 are indicated with the identical reference characters, and their explanations are omitted. The rays of light from the luminous element array 320, which is scanned by a drive circuit 1100 under the control of the micro processor 105, is detected by the detector 324 through an optical system 1000, as shown in FIG. 28. The signal from the detector 324 is fed, as in FIG. 22, through the analog switch 104 and the A/D converter 107 to the microprocessor 105. The microprocessor 105 locates the luminous points of the luminous element array 320 from the output of the detector 324 to calculate the straight-line loci from the luminous points so that the radii of curvature of the cornea can be calculated on the basis of these straight-line loci.

A laser beam can also be used as the luminous element array instead of using the light-emitting diodes as the luminous units of the array.

FIG. 29 shows a first example, in which a laser beam 501 from a GaAs semiconductor laser 500 is used for the scanning using laser scanning means 502 which uses a rotary polygonal mirror, a galvanometer reflecting mirror or an acoustic optical element. The laser beam is introduced into the optical fiber rods 504a which are arranged on the front of an optical fiber assembly 504 which has a collimator lens 503 at its back. The first embodiment thus constructed converts the laser beam into diffused beams by making use of the fact that a optical fiber rod has a large numerical aperture.

A rotary disc 512, which has a number of optical fibers 510 arranged in a straight line at one end thereof, and which has a laser beam guide optical system 511 at its other end that has the optical fibers bundled into a cylindrical end can be used instead of the linear luminous element array, shown in FIG. 30, and it is rotated by the action of a pulse motor 311 thereby to use the laser beam from the semiconductor laser 512 for the scanning purpose.

FIG. 31 is a view showing the optical arrangement of an embodiment in which the first measurement principle of the present invention is applied to a radius meter for measuring the base curve or the front curve of a contact lens. The constructional components similar to those of the first embodiment are indicated by identical reference numerals, and their explanations are omitted.

When the base curve of a contact lens CL is to be measured, the contact lens is so held in a cylindrical protrusion 601 of holding means as to have its convex facing downward.

A reflecting mirror 602 which has a similar action to that of the reflecting mirror of FIG. 12 is fitted at the bottom of the cylindrical protrusions. Thus, before the contact lens CL is held by the means 600, the reference coordinate system can be set by using the reflecting mirror 602.

In the present embodiment, incidentally, the conjugate planes D and D' of the position sensor 13 projected by the relay lens 14 are so designed that they are positioned inside the rear focal length $f_{CL}$ of the contact lens being measured.

It is needless to say that not only the first principle of the present invention but also the second and third measurement principles can be applied to the radius meter, although only the first is disclosed in the present embodiment.

The mask means of the measurement principles and the embodiments thus far described are directed to the example, in which they are formed with the straight-line aperture for selectively transmitting rays of light. However, it is needless to say that the use of a reflective straight-line pattern for selectively reflecting rays of light instead of that example can lead to the same operational effect to that of the present invention.

It is apparent that the circuit for scanning and driving the luminous elements or the light-receiving elements thereby to process the detected data arithmetically should not be limited to the above circuits but may be any circuit that can produce the necessary data and operate the above arithmetic equations, and can be designed in various manners by those skilled in the art.

I claim:

1. A curvature measuring apparatus comprising:
an illuminating optical system for illuminating a surface to be measured, said illuminating optical system including light source means forming a pattern of radiating beams of at least two groups, each group being composed of at least two parallel straight lines in a virtual plane, the straight lines in one group being different in directions of arrangement from the straight lines in the other group, each group including at least one line whose characteristics are substantially different from the other lines in the group to serve as a reference line, and collimator lens means for orienting principal rays of illuminating beams of light emitted from said light source means through a pin hole aranged on an optical axis, to be parallel to said optical axis so as to illuminate said surface to be measured by said illuminating beams of light;
detecting means positioned in a virtual plane which is afocal with the plane containing said light source means for detecting said illuminating beams of light reflected from said surface; and
arithmetic means for calculating a radius of curvature of said surface from changes in inclination and pitch which are produced between a pattern of projected straight-lines and said pattern of radiating beams from said light source means.

2. A curvature measuring apparatus as set forth in claim 1, wherein at least one of the straight lines constituting said groups of parallel straight lines is made different in at least one of thickness, number and luminous intensity from the others.

3. A curvature measuring apparatus as set forth in claim 2, said detecting means positioned in an afocal plane closer than the focal plane conjugate with the light source whereby the optical path is shortened.

4. A curvature measuring apparatus as set forth in claim 2, wherein said illuminating beams of light are infrared light.

5. A curvature measuring apparatus as set forth in claim 1, wherein said detecting means is a plane position sensor.

6. A curvature measuring apparatus as set forth in claim 3, wherein said detecting means is at least two linear position sensors which substantially intersect in said afocal plane.

7. A curvature measuring apparatus as set forth in claim 1, wherein said detecting means is at least two linear position sensors which are substantially parallel in said afocal plane.

8. A curvature measuring apparatus as set forth in claim 1, wherein said detecting means is at least one linear position sensor which is rotatable in said afocal plane.

9. A curvature measuring apparatus as set forth in claim 1, wherein said detecting means is at least one linear position sensor, and wherein light-rotating means is included for rotating said beams reflected from said surface being measured about the optical axis of said apparatus.

10. A curvature measuring apparatus as set forth in claim 1, wherein said detecting means is at least one linear position sensor which is movable parallelly in said afocal plane.

11. A curvature measuring apparatus as set forth in claim 1, wherein said detecting means is at least one linear position sensor and which includes light-shifting means for moving said reflected beams in a plane which is perpendicular to the optical axis of said apparatus.

12. A curvature measuring apparatus as set forth in claim 3, further comprising relay optical means for focusing said detecting means in said afocal plane.

13. A curvature measuring apparatus as set forth in claim 1, further comprising optical-path transforming means interposed between said surface being measured and said detecting means.

14. A curvature measuring apparatus as set forth in claim 1, further comprising a reflecting member having a reflecting face which is perpendicular to said illuminating optical axis and arranged to be inserted into the space between said surface being measured and said detecting means.

15. A curvature measuring apparatus as set forth in claim 12, wherein the optical axis of said relay optical means and said illuminating optical axis are made at least partially common.

16. A curvature measuring apparatus comprising:
an illuminating light source including a plurality of luminous units arranged in an identical virtual plane for irradiating a surface being measured;
optical detecting means, said optical detecting means including a detecting pattern of at least two groups, each group being consistuted by at least two parallel straight lines, said straight lines in one group being arranged in a direction which is different from the direction in which the straight lines in the other group are directed, each group including at least one line whose characteristics are substantially different from the other lines in the group to serve as a reference line, an optical detecting system having an optical axis and including an optical element for directing rays of light emitted from said illuminating light source and reflected parallel to said optical axis by said surface being measured toward said optical detecting means through a pin hole which is arranged on said optical axis; and arithmetic means for calcuating a radius of curvature of said surface being measured from changes in inclination and pitch which are produced between a straight line pattern formed by the luminous units of said light source and said detecting pattern of said optical detecting means.

17. A curvature measuring apparatus as set forth in claim 16, said detecting means being positioned in a virtual plane which is afocal with the plane containing said illuminating light source, whereby the optical path between said detecting means and the light illuminating means is shortened.

18. A curvature measuring apparatus as set forth in claim 16, wherein the rays of light emitted by said illuminating light source are infrared light.

19. A curvature measuring apparatus as set forth in claim 17, wherein said illuminating light source is at least two linear luminous-element arrays which substantially intersect in said afocal plane.

20. A curvature measuring apparatus as set forth in claim 17, wherein said illuminating light source is at least two linear luminous-element arrays which are substantially parallel in said afocal plane.

21. A curvature measuring apparatus as set forth in claim 17, wherein said illuminating light source is at least one linear luminous-element array which is rotatable in said afocal plane.

22. A curvature measuring apparatus as set forth in claim 17, wherein said illuminating light source is at least one linear luminous-element array, and wherein a luminous-flux rotating means is included for rotating the light beams emitted from said luminous-element array toward said surface being measured about the optical axis of said apparatus.

23. A curvature measuring apparatus as set forth in claim 17, wherein said illuminating light source is at least one linear luminous-element array which is movable parallelly in said afocal plane.

24. A curvature measuring apparatus as set forth in claim 17, wherein said illuminating light source is at least one linear luminous-element array and wherein luminous-flux shifting means is included for shifting the rays of light emitted from said luminous-element array toward said surface being measured, parallelly in a plane which is perpendicular to the optical axis of said apparatus.

25. A curvature measuring apparatus as set forth in claim 17, further comprising relay optical means for focusing said illuminating light source in said afocal plane.

26. A curvature measuring apparatus as set forth in claim 16, further comprising optical-path transforming means interposed between said surface being measured and said illuminating light source.

27. A curvature measuring apparatus as set forth in claim 26, wherein the optical axis of said relay optical means and the optical axis of said optical detecting system are made at least partially common.

28. A curvature measuring apparatus comprising:

an illuminating optical system including a light source and collimator means for collimating beams of light from said light source into parallel beams and directing the parallel beams toward a surface to be measured;

mask means having a selecting pattern constituted by at least two groups of straight lines, each group being composed of at least two parallel straight lines in a virtual plane so as to select beams of light from said illuminating optical system which are reflected by the surface being measured, the straight lines in one group being directed in a direction which is different from the direction in which the straight lines in the other group are directed, each group including at least one line whose characteristics are substantially different from the other lines in the group to serve as a reference line;

detecting means for detecting the beams of light selected by said mask means; and arithmetic means for calculating a radius of curvature of said surface being measured from changes in inclination and pitch between a pattern of projected straight-lines and said selecting pattern of said mask means;

said mask means and said detecting means being respectively arranged in different planes which are not optically conjugate with said light source.

29. A curvature measuring apparatus comprising:

an illuminating light source including a plurality bf luminous units;

mask means including at least two groups of straight lines, each group being composed of at least two parallel straight lines in a virtual plane so as to select beams of light emitted from said illuminating light source, the straight lines in one group being arranged in a direction which is different from the direction in which the straight lines in the other group are arranged, each group including at least one line whose characteristics are substantially different from the other lines in the group to serve as a reference line;

condensing means for introducing beams of light from said illuminting light source selected by said mask means and reflected by the surface being measured into pin-hole means;

detecting means for detecting the beams of light which have passed through said pin-hole means; and arithmetic means for calculating a radius of curvature of said surface being measured from changes in pitch and inclination between the straight lines produced by said luminous units and said selecting pattern of said mask means;

said mask means and said illuminating light source being respectively aranged in different planes which are not opitcally conjugate with said pin-hole means.

* * * * *